US011965201B2

United States Patent
Valgepea et al.

(10) Patent No.: US 11,965,201 B2
(45) Date of Patent: *Apr. 23, 2024

(54) ARGININE SUPPLEMENTATION TO IMPROVE EFFICIENCY IN GAS FERMENTING ACETOGENS

(71) Applicant: LanzaTech NZ, Inc., Skokie, IL (US)

(72) Inventors: Kaspar Valgepea, Brisbane (AU); Michael Koepke, Chicago, IL (US); James Bruce Yarnton Haycock Behrendorff, Frederiksberg (DK); Esteban Marcellin, Brisbane (AU); Lars K. Nielsen, Brisbane (AU); Renato de S. P. Lemgruber, Brisbane (AU)

(73) Assignee: LanzaTech NZ, Inc., Skokie, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/203,617

(22) Filed: Mar. 16, 2021

(65) Prior Publication Data

US 2021/0230648 A1 Jul. 29, 2021

Related U.S. Application Data

(63) Continuation of application No. 15/368,521, filed on Dec. 2, 2016, now Pat. No. 10,995,347.

(60) Provisional application No. 62/262,886, filed on Dec. 3, 2015, provisional application No. 62/262,888, filed on Dec. 3, 2015.

(51) Int. Cl.
| | |
|---|---|
| *C12P 7/56* | (2006.01) |
| *C12N 1/20* | (2006.01) |
| *C12N 1/38* | (2006.01) |
| *C12N 9/06* | (2006.01) |
| *C12N 9/10* | (2006.01) |
| *C12N 9/12* | (2006.01) |
| *C12N 9/78* | (2006.01) |
| *C12N 9/90* | (2006.01) |
| *C12N 15/52* | (2006.01) |
| *C12P 7/04* | (2006.01) |
| *C12P 7/06* | (2006.01) |
| *C12P 7/18* | (2006.01) |
| *C12P 7/40* | (2006.01) |
| *C12P 7/54* | (2006.01) |

(52) U.S. Cl.
CPC .............. *C12P 7/56* (2013.01); *C12N 1/20* (2013.01); *C12N 1/38* (2013.01); *C12N 9/0016* (2013.01); *C12N 9/1018* (2013.01); *C12N 9/1029* (2013.01); *C12N 9/1217* (2013.01); *C12N 9/78* (2013.01); *C12N 9/90* (2013.01); *C12N 15/52* (2013.01); *C12P 7/04* (2013.01); *C12P 7/065* (2013.01); *C12P 7/18* (2013.01); *C12P 7/40* (2013.01); *C12P 7/54* (2013.01); *C12Y 104/01012* (2013.01); *C12Y 201/03003* (2013.01); *C12Y 207/02002* (2013.01); *C12Y 305/03006* (2013.01); *C12Y 501/01012* (2013.01); *C12Y 504/03005* (2013.01); *Y02E 50/10* (2013.01)

(58) Field of Classification Search
CPC .... C12P 7/56; C12P 7/04; C12P 7/065; C12P 7/18; C12P 7/40; C12P 7/54; C12P 1/04; C12N 1/20; C12N 1/38; C12N 9/0016; C12N 9/1018; C12N 9/1029; C12N 9/1217; C12N 9/78; C12N 9/90; C12N 15/52; C12Y 104/01012; C12Y 201/03003; C12Y 207/02002; C12Y 305/03006; C12Y 501/01012; C12Y 504/03005; Y02E 50/10
See application file for complete search history.

(56) References Cited

U.S. PATENT DOCUMENTS

2003/0092099 A1* 5/2003 Clark ............. C12Y 305/03006 435/254.2

FOREIGN PATENT DOCUMENTS

WO WO2013180584 A1 * 12/2013

OTHER PUBLICATIONS

Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10: 8-9. (Year: 2002).*
Shin et al. Metabolic engineering of microorganisms for the production of L-arginine and its derivatives. Microbial Cell Factories 2014, 13: p166 (internal p. 1-11. (Year: 2014).*
Kupas et al., "Large scale analysis of protein-binding cavities using self-organizing maps and wavelet-based surface patches to describe functional properties, selectivity discrimination, and putative cross-reactivity" Proteins, Nov. 27, 2007, Wiley InterScience, pp. 1288-1306. DOI: 10.1002/prot.21823.

* cited by examiner

*Primary Examiner* — Iqbal H Chowdhury

(57) ABSTRACT

The invention provides methods for improving efficiency of fermentation by arginine supplementation, and genetically modified bacterium for use therefor. More particularly the invention provides methods for (i) increasing the production ATP intensive products with arginine supplementation, (ii) increasing utilization of arginine by a C1-fixing bacterium; and (iii) providing C1-fixing bacterium with optimized arginine de-aminase pathways.

6 Claims, 14 Drawing Sheets

With (△) and without (●) arginine supplementation (n = 3, mean ± SD)

With (△) arginine; without (●) arginine; arginine only (□) (n = 3, mean ± SD)

C. autoethanogenum DSM 23693 with (△) and without (●) arginine supplementation

4AA

ARG

ARGININE SUPPLEMENTATION TO IMPROVE EFFICIENCY IN GAS FERMENTING ACETOGENS

CROSS REFERENCE TO RELATED APPLICATIONS

This application is a continuation of U.S. Pat. No. 10,995,347 issued May 4, 2021, which claims the benefit of U.S. Provisional Patent Application Nos. 62/262,886 filed Dec. 3, 2015, and 62/262,888 filed Dec. 3, 2015, the entirety of which is incorporated herein by reference.

BACKGROUND OF THE INVENTION

Approximately 10% of the world's energy demand and commodity chemicals are currently produced from renewable feedstocks, primarily using farmed sugars. However there is an increasing focus on the future use of non-food resources to meet climate targets. Gas fermentation offers a route to use a wide range of readily available, low cost C1 feedstocks such as industrial waste gases, syngas or reformed methane into chemicals and fuels. Believed to be one of the first biochemical pathways to emerge on earth, the Wood Ljungdahl pathway enables acetogenic Clostridia to fix these C1 gases into acetyl-CoA. *Clostridium autoethanogenum*, in particular, offers a robust and flexible platform for gas fermentation and has been deployed at industrial scale. Fermentation of gas by *C. autoethanogenum* is highly selective, tolerates contaminants, resolves refractiveness of the Fischer-Tropsch processes and is economically viable even when supplied with small volume gas streams.

It is known, that whilst acetogens are capable of producing many useful short-chain chemicals, the production of longer-chain carbon molecules for use in biodiesel or jet fuels is outside the metabolic capacity of acetogenic bacteria on their own, due to ATP limitation. Fast et al determined that whilst the Wood Ljungdahl pathway was the best performing pathway for acetate and ethanol production, butanol fermentation is an ATP-limited process, making anaerobic production of butanol from the Wood Ljungdahl pathway inefficient.

*C. autoethanogenum* natively produces acetate, ethanol, 2,3-Butanediol (2,3-BDO) and lactate. If energetic impediments can be overcome, synthetic biology promises to enhance the product spectrum of *C. autoethanogenum*. Acetogenic bacteria are widespread in nature and play a major role in global carbon cycle, but are considered to live on the thermodynamic edge of life.

Energetics of the Wood-Ljungdahl pathway of anaerobic acetogens are just emerging, but unlike under aerobic growth conditions or glycolysis of sugar fermenting organisms no ATP is gained in the Wood-Ljungdahl pathway by substrate level phosphorylation, in fact, activation of $CO_2$ to formate actually requires one molecule of ATP and a membrane gradient is required. [WO 2013/180584].

ATP generation through substrate level phosphorylation can be used as a driving force for product synthesis, especially in ATP-limited systems. In particular, acetogenic bacteria are known to live on the thermodynamic edge of life (Schuchmann, Nat Rev Microbiol, 12: 809-821, 2014). As such, all acetogenic microorganisms isolated to date have been described to produce acetate (Drake, Acetogenic Prokaryotes, In: The Prokaryotes, 3rd edition, pages 354-420, New York, NY, Springer, 2006; Liew et al, Insights into CO2 Fixation Pathway of *Clostridium autoethanogenum* by Targeted Mutagenesis. mBio, 2016, 7: e00427-16) since the production of acetate provides the microorganism with an option to directly generate ATP from substrate level phosphorylation via Pta (phosphotransacetylase) (EC 2.3.1.8) and Ack (acetate kinase) (EC 2.7.2.1). The Pta-Ack system is highly specific to acetyl-CoA conversion to acetate and not utilizing other acyl-CoAs. Although mechanisms such as membrane gradients and electron bifurcation enzymes coupled to ion or proton translocating systems, e.g., the Rnf complex (Schuchmann, Nat Rev Microbiol, 12: 809-821, 2014), conserve ATP in these microorganisms, direct ATP generation remains critical for their survival. As a result, when introducing heterologous pathways that do not allow for ATP generation, acetate is produced as a by-product (Schiel-Bengelsdorf, FEBS Lett, 586: 2191-2198, 2012).

SUMMARY OF THE INVENTION

The invention provides a method for improving the efficiency of fermentation, the method comprising, flowing a gaseous C1 containing substrate to a bioreactor containing a culture of one or more C1 fixing microorganisms in a liquid nutrient media; and fermenting the culture to produce at least one product. Arginine is provided to the culture in excess of the requirements for synthesis of biomass. Generally, the C1 fixing microorganism comprises an arginine metabolism pathway.

In a second aspect, the invention provides a method for increasing the production of at least one ATP intensive product, the method comprising; flowing a gaseous C1 containing substrate to a bioreactor containing a culture of one or more C1 fixing microorganisms in a liquid nutrient media; and fermenting the culture to produce at least one product. In certain embodiments, arginine is provided to the culture in excess of the requirements for synthesis of biomass and the C1 fixing microorganism comprises an arginine metabolism pathway.

In particular embodiments, the arginine metabolism pathway comprises at least one of an arginine deaminase pathway and an arginine decarboxylase pathway. The arginine deaminase pathway comprises one or more enzymes selected from the group consisting of arginine deiminase (EC 3.5.3.6), ornithine carbomyltransferase (putrescine carbomyltransferase) (EC 2.1.3.3) and a carbamate kinase (EC 2.7.2.2). The arginine decarboxylase pathway comprises one or more enzymes selected from the group consisting arginine decarboxylase (EC 4.1.1.19), putative arginine deaminase (EC 3.5.3.12), putrescine carbamoyl transferase (EC 2.1.3.6) and carbamate kinase (EC 2.7.2.2).

Generally the amount of arginine provided to the culture of C1-fixing microorganism is in excess of the requirement for synthesis of biomass. In certain embodiments arginine is provided to the culture is at about the cellular requirement to about 1000 times above the cellular requirements. In certain embodiments arginine is provided to the culture at from 2 to 1000 or from 2 to 800 or from 2 to 500 or from 2 to 100 or from 2 to 50 or from 2 to 10 or from 50 to 1000, or from 50 to 800, or from 50 to 600, or from 50 to 500, or from 50 to 300 or from 50 to 200, or from 50 to 100 or from 100 to 1000 or from 100 to 800 or from 100 to 600 or from 100 to 500 or from 100 to 300 or from 100 to 200 times the cellular requirement.

According to certain embodiments, arginine is provided to the culture, such that the concentration of arginine is maintained at an amount of at least 20 mg/L, or at least 100 mg/L or at least 300 mg/L or at least 500 mg/L, or at least 1 g/L or at least 2 g/l, or at least 3 g/l, or at least 4 g/L or at least 5 g/L or at least 10 g/L, or at least 20 g/L. In certain embodiments, the concentration of arginine is maintained at between 20 mg/L to about 20 g/l. or between 100 mg/L to 20 g/L, or between 500 mg/l to 20 g/L, or between 500 mg/L to 10 g/L, or between 1 g/L to 10 g/L or between 5 g/L to 10 g/L, or between 5 g/L to 20 g/L. In certain embodiment's arginine is provided to the culture such that arginine consumption by the culture was at least 20 mg arginine per gram of dry cell weight or at least 100 mg arginine per gram of dry cell weight, or at least 1 grams arginine per gram of dry cell weight, or at least 5 grams arginine per gram of dry cell weight, or at least 10 grams arginine per gram of dry cell weight. In certain embodiments, arginine is provided to the culture such that arginine consumption by the culture is between 20 mg to 20 grams per gram of dry cell weight, or between 100 mg and 20 grams per gram of dry cell weight, or between 1 gram and 10 grams per gram of dry cell weight.

In certain embodiments at least 0.012 g arginine is consumed by the culture to produce 1 g biomass. In certain embodiments, the cellular requirement of arginine for biomass synthesis is between 0.012 g per gram biomass to about 24 g per gram biomass. In certain embodiments the arginine requirement for biomass synthesis is at least 0.012 g per gram biomass, or at least 0.024 g per gram biomass, to about 0.048 g per gram biomass, or least 0.120 g per gram biomass, or at least 0.24 g per gram biomass, or at least 0.48 g per gram biomass, or at least 1.2 g per gram biomass, or at least 2.4 g per gram biomass, or at least 4.8 g per gram biomass, or at least 12 g per gram biomass.

Generally, arginine is provided to the culture of C1 fixing microorganism as a component of the liquid nutrient medium that is continuously fed to the bioreactor. In other embodiments, arginine is provided to the bioreactor independently of the liquid nutrient medium (e.g. by continuous feed or dosing).

In certain embodiments the doubling time of the culture is increased by at least 10%, or at least 20%, or at least 30%, or at least 40%, or at least 50%, or at least 60%, or at least 70% when arginine is provided to the culture in excess of the cellular requirements of the microorganism, compared to a culture where arginine is not provided in excess of the cellular requirements of the culture.

In particular embodiments, the C1 fixing microorganism comprises at least one of an arginine deiminase pathway or an arginine decarboxylase pathways.

In particular embodiments, the C1 fixing microorganism is an acetogenic carboxydotrophic microorganism. Examples of suitable C1-fixing microorganisms include *Clostridium, Moorella, Oxobacter, Peptostreptococcus, Acetobacterium, Eubacterium*, or *Butyribacterium*. In various embodiments, the microorganism is selected from the group comprising *Clostridium autoethanogenum, Clostridium ljungdahlii, Clostridium carboxidivorans, Clostridium drakei, Clostridium scatologenes, Clostridium aceticum, Clostridium formicoaceticum, Clostridium magnum, Clostridium ragsdalei, Clostridium coskatii, Butyribacterium methylotrophicum, Acetobacterium woodii, Alkalibaculum bacchi, Blautia producta, Eubacterium limosum, Moorella thermoacetica, Sporomusa ovata, Sporomusa silvacetica, Sporomusa sphaeroides, Oxobacter pfennigii* and *Thermoanaerobacter kiuvi*.

In particular embodiments, the C1-fixing microorganism is *Clostridium autoethanogenum* or *Clostridium ljungdahlii*. In one particular embodiment, the microorganism is *Clostridium autoethanogenum*. In a particular embodiments, the bacterium has the identifying characteristics of accession number DSM10061, DSM19630 or DSM23693. These bacteria have been deposited at the German Resource Centre for Biological Material (DSMZ) whose address is DSMZ GmbH Inhoffenstraße, 7 B, D-38124.

In certain embodiments, the C1-fixing microorganism is selected from the group consisting of *Clostridium autoethanogenum, Clostridium ljungdahlii, Clostridium scatologenes, Clostridium drakei*, and *Acetonema longum*.

The at least one product can be any product that is made by either native or recombinant C1-fixing microorganisms. In certain embodiments the at least one product is selected from the group consisting of ethanol, 2,3-butanediol, 1,3-butanediol, lactate, succinate, methyl ethyl ketone (MEK), butyrate, 2-butanol, 1,2-propanediol (1,2-PDO), 1-propanol, isopropanol (IPA), acetoin, iso-butanol, isoprene, farnesene, bisabolene, pinine, limonene, acetone, 3-hydroxybutyrate, 2-hydroxyisobutyric acid (2-HIBA), citramalate, butadiene, poly lactic acid, 1-butanol, 3-hydroxy propionate (3-HP), benzoate, fatty acid ethyl ester, and fatty acids, isobutylene.

In particular embodiments, the concentration of arginine provided to the culture is increased in order to increase the production of at least one ATP-intensive product. Generally the rate of production of the at least one ATP intensive product is at least 1.5 times greater than the rate of production of the at least one ATP intensive product when arginine is not provided in excess to cellular requirements of the culture. In certain embodiments, the rate of production of the at least one ATP intensive product is at least 2 times greater, or at least 3 times greater, or at least 4 times greater, or at least 5 times greater, or at least 10 times greater.

ATP intensive products are generally defined as products that either have a direct ATP requirement in the metabolic pathway. Examples of ATP intensive products (products that directly require ATP for synthesis having an ATP-dependent reaction in the pathway) include but are not limited to Terpenoides/Mevalonate pathway derived products including isoprene, farnesene, bisabolene, and limonene, Fatty acid pathway derived products including Fatty acids, fatty acid ethyl esters or molecules such as 3-hydroxy propionate (3-HP) or isobutylene.

In particular embodiments, the concentration of arginine provided to the culture is increased in order to increase the production of at least one product selected from a group of products that do not directly require ATP but also do not yield the same amount of ATP per acetyl-CoA as the formation of acetate. In certain embodiments the concentration of arginine provided to the culture is increased in order to increase the production of at least one product selected from the group consisting of Acetone, IPA, 3-1113, 2-HIBA, 1,3-BDO, 2,3-BDO, Lactate, 1,2-PDO, 1-Propanol, isobutaneol, Butyrate, Butanol, Citramalate, Succinate, and MEK.

In preferred embodiments, the culture produces reduced amount of acetate compared to a culture where arginine is not provided in excess to cellular requirements. In certain embodiments the culture produces at least 10% less acetate, or at least 20% less acetate, or at least 30% less acetate, or at least 40% less acetate, or at least 50% less acetate, or at least 60% less acetate, or at least 80% less acetate. In certain embodiments no net acetate is produced less than 1 g/L acetate, less than 0.5 g/L acetate, less than 0.1 g/L acetate, less than 0.05 g/L acetate, or less than 0.01 g/L acetate.

The invention further provides a method for improving efficiency of a fermentation, the method comprising providing the culture with one or more gaseous substrates and arginine, and fermenting the culture such that the culture utilizes argine and the one or more gaseous substrates. In particular embodiments the gaseous substrate is selected from the group consisting of CO, $H_2$ and $CO_2$. In particular embodiments arginine and the gaseous substrate are taken up by the culture at a ratio of at least 2:1, or at least 1:1, or at least 1:2.

In a third aspect, the invention provides a method for improving the sustainability of a fermentation process, the method comprising flowing a gaseous C1 containing substrate to a bioreactor containing a culture of at least one C1 fixing bacterium comprising at least one of an arginine deiminase pathway or an arginine decarboxylase pathway in a liquid nutrient media; and fermenting the culture to produce at least one product. In certain embodiments, arginine is provided to the culture in excess of the cellular requirements of the culture. In certain embodiments, arginine provided to the culture is catabolized by the arginine deiminase pathway to produce ammonium, which is utilized by the culture as a nitrogen source.

The invention further provides a method of growth of a C1-fixing bacterium with arginine as the sole nitrogen source. In particular embodiments, arginine is provided to the culture and no ammonium is extrinsically provided to the culture.

The C1 fixing bacterium may be selected from the group consisting of *Clostridium, Moorella, Eubacterium,* Oxobacter, *Sporomusa* and *Thermoanaerobacter*. In certain embodiments the bacterium is selected from the group consisting of *Acetobacterium woodii, Alkalibaculum bacchii, Blautia* product, *Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides, Thermoanaerobacter kiuvi*. In preferred embodiments, the bacterium is selected from the group consisting of *Clostridium autoethanogenum, Clostridium ljungdahlii, Clostridium* ragsdalei and *Clostridium coskatii*.

Another aspect of the invention further provides a genetically engineered C1-fixing bacterium comprising an optimized arginine deiminase pathway. In one embodiment the invention provides a genetically engineered C1-fixing bacterium comprising one or more enzymes selected from the group consisting of: arginine deiminase (EC 3.5.3.6), carbomyltransferase (ornithine carbomyltransferase, putrescine carbomyltransferase) (EC 2.1.3.3), and carbamate kinase (EC 2.7.2.2), wherein each enzyme is an overexpressed endogenous enzyme, a mutated endogenous enzyme or an exogenous enzyme. In particular embodiments, the C1-fixing bacterium is a *Clostridium* bacterium. In particular embodiments, the bacterium is *Clostridium autoethanogenum*.

The invention further provides a genetically engineered C1-fixing bacterium having improved cellular metabolism of arginine compared to a parental microorganism, wherein the genetically engineered C1-fixing bacterium comprises one or more genetic modification which disrupts an arginine transporter. In particular embodiments, the genetic modification is a knock-out or replacement of the arginine:ornithine transporter (CAETHG_3023-24). In certain embodiments, the bacterium further comprises one or more enzymes selected from the group consisting of arginine deiminase (EC 3.5.3.6), ornithine carbomyltransferase (putrescine carbomyltransferase) (EC 2.1.3.3), a carbamate kinase (EC 2.7.2.2), ornithine racemase (EC 5.1.1.12), ornithine aminomutase (EC 5.4.3.5), 2,4-diaminopentanoate dehydrogenase (EC 1.4.1.12), 2-amino-4-oxopentanoate Thiolase (EC 2.3.1.B10), wherein each enzyme is an overexpressed endogenous enzyme, a mutated endogenous enzyme or an exogenous enzyme.

The invention further provides a method for producing at least one product from a substrate, the method comprising culturing a genetically engineered C1-fixing bacterium comprising one or more enzymes selected from the group consisting of: arginine deiminase (EC 3.5.3.6), carbomyltransferase (ornithine carbomyltransferase, putrescine carbomyltransferase) (EC 2.1.3.3), and carbamate kinase (EC 2.7.2.2), wherein each enzyme is an overexpressed endogenous enzyme, a mutated endogenous enzyme of an exogenous enzyme.

The invention further provides a method for improving efficiency of arginine incorporation into the metabolism, the method comprising culturing a genetically engineered C1-fixing bacterium comprising one or more genetic modifications selected from the group consisting of (i) a disruptive mutation which disrupts an arginine transporter; (ii) overexpression of one or more endogenous enzymes selected from the group consisting of arginine deiminase (EC 3.5.3.6), ornithine carbomyltransferase (putrescine carbomyltransferase) (EC 2.1.3.3), carbamate kinase (EC 2.7.2.2), ornithine racemase (EC 5.1.1.12), ornithine aminomutase (EC 5.4.3.5), 2,4-diaminopentanoate dehydrogenase (EC 1.4.1.12), and 2-amino-4-oxopentanoate Thiolase (EC 2.3.1.B10 (iii) expression of one or more mutated endogenous enzymes selected from the group consisting of arginine deiminase (EC 3.5.3.6), ornithine carbomyltransferase (putrescine carbomyltransferase) (EC 2.1.3.3), carbamate kinase (EC 2.7.2.2), ornithine racemase (EC 5.1.1.12), ornithine aminomutase (EC 5.4.3.5), 2,4-diaminopentanoate dehydrogenase (EC 1.4.1.12), and 2-amino-4-oxopentanoate Thiolase (EC 2.3.1.B10) and (iv) expression of one or more exogenous enzymes selected from the group consisting of arginine deiminase (EC 3.5.3.6), ornithine carbomyltransferase (putrescine carbomyltransferase) (EC 2.1.3.3), carbamate kinase (EC 2.7.2.2), ornithine racemase (EC 5.1.1.12), ornithine aminomutase (EC 5.4.3.5), 2,4-diaminopentanoate dehydrogenase (EC 1.4.1.12), and 2-amino-4-oxopentanoate Thiolase (EC 2.3.1.B10)

The invention further provides a method for improving efficiency of arginine co-utilization with one or more gaseous substrates selected from the group consisting of CO, $H_2$ and $CO_2$, the method comprising culturing a genetically engineered C1-fixing bacterium comprising one or more genetic modifications, wherein the one or more genetic modifications are selected from the group consisting of (i) the disruptive mutation of regulatory elements and (ii) the replacement of operator binding sites or native promoters with constitutive or synthetic promoters. In particular embodiments, the disruptive mutation is a knock-out of arginine repressor argR, and the replacement is a replacement of an arginine deiminase pathway operon promoter with a constitutive or synthetic promoter.

DETAILED DESCRIPTION OF THE INVENTION

Definitions and Background

Figure 1:
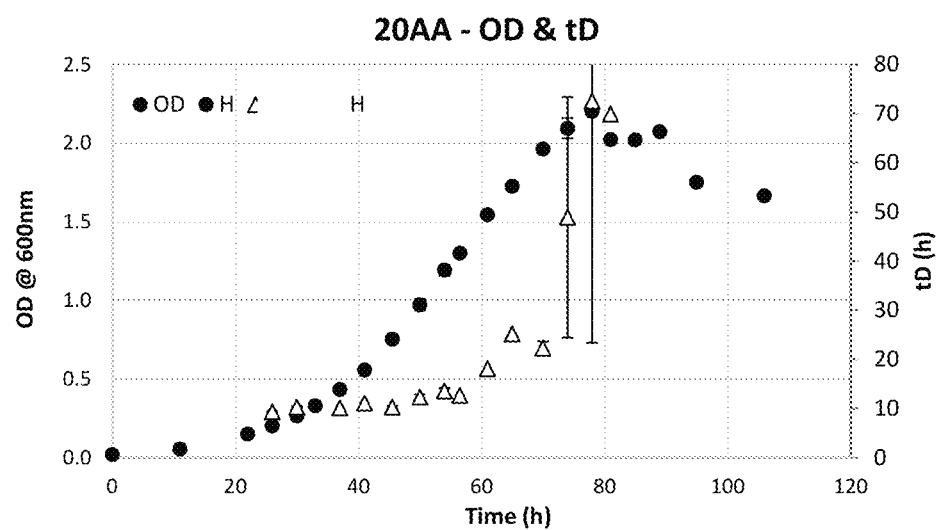
FIG. 1 is a graph showing growth of *C. autoethanogenum* DSM10061 in 20-amino acid defined medium+5 g fructose/L.

The term "in excess of cellular requirements" refers to providing a component to the microorganism which is greater than the amount of the component that is required by the microorganism for biomass synthesis.

The term "ATP intensive product" refers to a metabolite which synthesis requires ATP (energy) input at least in one step of its synthesis pathway (e.g. having an ATP-dependent reaction in the pathway).

The term "specific growth rate" refers to the rate of cell biomass growth per cell biomass per hour.

The term "doubling time" refers to the time in hours it takes cell biomass to double.

The term "arginine metabolism pathway" broadly refers to any pathway involved in the metabolism of arginine. The arginine metabolism pathway typically comprises at least one of an arginine deiminase pathway and an arginine decarboxylase pathway.

The term "genetic modification" or "genetic engineering" broadly refers to the manipulation of the genome or nucleic acids of a microorganism. Likewise, the term "genetically engineered" refers to a microorganism comprising a manipulated genome or nucleic acids. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

"Recombinant" indicates that a nucleic acid, protein, or microorganism is the product of genetic modification, engineering, or recombination. Generally, the term "recombinant" refers to a nucleic acid, protein, or microorganism that contains or is encoded by genetic material derived from multiple sources, such as two or more different strains or species of microorganisms. As used herein, the term "recombinant" may also be used to describe a microorganism that comprises a mutated nucleic acid or protein, including a mutated form of an endogenous nucleic acid or protein.

"Endogenous" refers to a nucleic acid or protein that is present or expressed in the wild-type or parental microorganism from which the microorganism of the invention is derived. For example, an endogenous gene is a gene that is natively present in the wild-type or parental microorganism from which the microorganism of the invention is derived. In one embodiment, the expression of an endogenous gene may be controlled by an exogenous regulatory element, such as an exogenous promoter.

"Exogenous" refers to a nucleic acid or protein that is not present in the wild-type or parental microorganism from which the microorganism of the invention is derived. In one embodiment, an exogenous gene or enzyme may be derived from a heterologous (i.e., different) strain or species and introduced to or expressed in the microorganism of the invention. In another embodiment, an exogenous gene or enzyme may be artificially or recombinantly created and introduced to or expressed in the microorganism of the invention. Exogenous nucleic acids may be adapted to integrate into the genome of the microorganism of the invention or to remain in an extra-chromosomal state in the microorganism of the invention, for example, in a plasmid.

"Enzyme activity," or simply "activity," refers broadly to enzymatic activity, including, but not limited, to the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" enzyme activity includes decreasing the activity of an enzyme, decreasing the amount of an enzyme, or decreasing the availability of an enzyme to catalyze a reaction.

"Mutated" refers to a nucleic acid or protein that has been modified in the microorganism of the invention compared to the wild-type or parental microorganism from which the microorganism of the invention is derived. In one embodiment, the mutation may be a deletion, insertion, or substitution in a gene encoding an enzyme. In another embodiment, the mutation may be a deletion, insertion, or substitution of one or more amino acids in an enzyme.

In particular, a "disruptive mutation" is a mutation that reduces or eliminates (i.e., "disrupts") the expression or activity of a gene or enzyme. The disruptive mutation may partially inactivate, fully inactivate, or delete the gene or enzyme. The disruptive mutation may be a knockout (KO) mutation. The disruptive mutation may be any mutation that reduces, prevents, or blocks the biosynthesis of a product produced by an enzyme. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, CRISPR) or protein which inhibits the expression of an enzyme. The disruptive mutation may be introduced using any method known in the art.

Introduction of a disruptive mutation results in a microorganism of the invention that produces no target product or substantially no target product or a reduced amount of target product compared to the parental microorganism from which the microorganism of the invention is derived. For example, the microorganism of the invention may produce no target product or at least about 1%, 3%, 5%, 10%, 20%, 30%, 40%, 50%, 60%, 70%, 80%, 90%, or 95% less target product than the parental microorganism. For example, the microorganism of the invention may produce less than about 0.001, 0.01, 0.10, 0.30, 0.50, or 1.0 g/L target product.

"Codon optimization" refers to the mutation of a nucleic acid, such as a gene, for optimized or improved translation of the nucleic acid in a particular strain or species. Codon optimization may result in faster translation rates or higher translation accuracy. In a preferred embodiment, the genes of the invention are codon optimized for expression in *Clostridium*, particularly *Clostridium autoethanogenum*, *Clostridium ljungdahlii*, or *Clostridium* ragsdalei. In a further preferred embodiment, the genes of the invention are codon optimized for expression in *Clostridium autoethanogenum* LZ1561, which is deposited under DSMZ accession number DSM23693.

"Overexpressed" refers to an increase in expression of a nucleic acid or protein in the microorganism of the invention compared to the wild-type or parental microorganism from which the microorganism of the invention is derived. Overexpression may be achieved by any means known in the art, including modifying gene copy number, gene transcription rate, gene translation rate, or enzyme degradation rate.

The term "variants" includes nucleic acids and proteins whose sequence varies from the sequence of a reference nucleic acid and protein, such as a sequence of a reference nucleic acid and protein disclosed in the prior art or exemplified herein. The invention may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants." By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *Clostridium acetobutylicum*, *Clostridium beijerinckii*, or *Clostridium ljungdahlii*, the details of which are publicly available on websites such as Genbank or NCBI. Functionally equivalent variants also include nucleic acids whose sequence varies as a result of codon optimization for a particular microorganism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

Nucleic acids may be delivered to a microorganism of the invention using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In a preferred embodiment, nucleic acids are delivered to the microorganism of the invention using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before the introduction of the nucleic acid into a microorganism.

Furthermore, nucleic acids may be designed to comprise a regulatory element, such as a promoter, to increase or otherwise control the expression of a particular nucleic acid. The promoter may be a constitutive promoter or an inducible promoter. Ideally, the promoter is a Wood-Ljungdahl pathway promoter, a ferredoxin promoter, a pyruvate:ferredoxin oxidoreductase promoter, an Rnf complex operon promoter, an ATP synthase operon promoter, or a phosphotransacetylase/acetate kinase operon promoter.

A "microorganism" is a microscopic organism, especially a bacterium, archaea, virus, or fungus. The microorganism of the invention is typically a bacterium. As used herein, recitation of "microorganism" should be taken to encompass "bacterium."

A "parental microorganism" is a microorganism used to generate a microorganism of the invention. The parental microorganism may be a naturally-occurring microorganism (i.e., a wild-type microorganism) or a microorganism that has been previously modified (i.e., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. The microorganism of the invention may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In a preferred embodiment, the parental microorganism is *Clostridium autoethanogenum* LZ1561, which was deposited on Jun. 7, 2010 with Deutsche Sammlung von Mikroorganismen und Zellkulturen GmbH (DSMZ) located at Inhoffenstraß 7B, D-38124 Braunschweig, Germany on Jun. 7, 2010 under the terms of the Budapest Treaty and accorded accession number DSM23693.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism. In one embodiment, the microorganism of the invention is derived from *Clostridium autoethanogenum*, *Clostridium ljungdahlii*, or *Clostridium ragsdalei*. In a preferred embodiment, the microorganism of the invention is derived from *Clostridium autoethanogenum* LZ1561, which is deposited under DSMZ accession number DSM23693.

The microorganism of the invention may be further classified based on functional characteristics. For example, the microorganism of the invention may be or may be derived from a C1-fixing microorganism, an anaerobe, an acetogen, an ethanologen, a carboxydotroph, and/or a methanotroph. Table 1 provides a representative list of microorganisms and identifies their functional characteristics.

TABLE 1

|  | C1-fixing | Anaerobe | Acetogen | Ethanologen | Autotroph | Carboxydotroph | Methanotroph |
|---|---|---|---|---|---|---|---|
| *Acetobacterium woodii* | + | + | + | +/− [1] | − | − | − |
| *Alkalibaculum bacchii* | + | + | + | + | + | + | − |
| *Blautia product* | + | + | + | − | + | + | − |
| *Butyribacterium methylotrophicum* | + | + | + | + | + | + | − |
| *Clostridium aceticum* | + | + | + | − | + | + | − |
| *Clostridium autoethanogenum* | + | + | + | + | + | + | − |
| *Clostridium carboxidivorans* | + | + | + | + | + | + | − |
| *Clostridium coskatii* | + | + | + | + | + | + | − |
| *Clostridium drakei* | + | + | + | − | + | + | − |
| *Clostridium formicoaceticum* | + | + | + | − | + | + | − |
| *Clostridium ljungdahlii* | + | + | + | + | + | + | − |
| *Clostridium magnum* | + | + | + | − | + | +/− [2] | − |
| *Clostridium ragsdalei* | + | + | + | + | + | + | − |
| *Clostridium scatologenes* | + | + | + | − | + | + | − |
| *Eubacterium limosum* | + | + | + | − | + | + | − |
| *Moorella thermautotrophica* | + | + | + | + | + | + | − |
| *Moorella thermoacetica* (formerly *Clostridium thermoaceticum*) | + | + | + | − [3] | + | + | − |
| *Oxobacter pfennigii* | + | + | + | − | + | + | − |
| *Sporomusa ovata* | + | + | + | − | + | +/− [4] | − |
| *Sporomusa silvacetica* | + | + | + | − | + | +/− [5] | − |
| *Sporomusa sphaeroides* | + | + | + | − | + | +/− [6] | − |
| *Thermoanaerobacter kiuvi* | + | + | + | − | + | − | − |

[1] *Acetobacterium woodi* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium. In a preferred embodiment, the microorganism of the invention is derived from a C1-fixing microorganism identified in Table 1.

An "anaerobe" is a microorganism that does not require oxygen for growth. An anaerobe may react negatively or even die if oxygen is present above a certain threshold. Typically, the microorganism of the invention is an anaerobe. In a preferred embodiment, the microorganism of the invention is derived from an anaerobe identified in Table 1.

An "acetogen" is an obligately anaerobic bacteria that use the Wood-Ljungdahl pathway as their main mechanism for energy conservation and for the synthesis of acetyl-CoA and acetyl-CoA-derived products, such as acetate (Ragsdale, Biochim Biophys Acta, 1784: 1873-1898, 2008). Acetogens use the acetyl-CoA pathway as a (1) mechanism for the reductive synthesis of acetyl-CoA from CO2, (2) terminal electron-accepting, energy conserving process, (3) mechanism for the fixation (assimilation) of CO2 in the synthesis of cell carbon (Drake, Acetogenic Prokaryotes, In: The Prokaryotes, 3rd edition, p. 354, New York, NY, 2006). All naturally occurring acetogens are C1-fixing, anaerobic, autotrophic, and non-methanotrophic. Typically, the microorganism of the invention is an acetogen. In a preferred embodiment, the microorganism of the invention is derived from an acetogen identified in Table 1.

An "ethanologen" is a microorganism that produces or is capable of producing ethanol. Typically, the microorganism of the invention is an ethanologen. In a preferred embodiment, the microorganism of the invention is derived from an ethanologen identified in Table 1.

An "autotroph" is a microorganism capable of growing in the absence of organic carbon. Instead, autotrophs use inorganic carbon sources, such as CO and/or CO2. Typically, the microorganism of the invention is an autotroph. In a preferred embodiment, the microorganism of the invention is derived from an autotroph identified in Table 1.

A "carboxydotroph" is a microorganism capable of utilizing CO as a sole source of carbon. Typically, the microorganism of the invention is a carboxydotroph. In a preferred embodiment, the microorganism of the invention is derived from a carboxydotroph identified in Table 1.

A "methanotroph" is a microorganism capable of utilizing methane as a sole source of carbon and energy. In certain embodiments, the microorganism of the invention is derived from a methanotroph.

More broadly, the microorganism of the invention may be derived from any genus or species identified in Table 1.

In a preferred embodiment, the microorganism of the invention is derived from the cluster of Clostridia comprising the species *Clostridium autoethanogenum*, *Clostridium ljungdahlii*, and *Clostridium ragsdalei*. These species were first reported and characterized by Abrini, *Arch Microbiol*, 161: 345-351, 1994 (*Clostridium autoethanogenum*), Tanner, *Int J System Bacteriol*, 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 µm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids to their corresponding alcohols has been shown in these species (Perez, *Biotechnol Bioeng*, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol*, 22: 320-325, 2011).

Thus, in summary, many of the characteristics of *Clostridium autoethanogenum*, *Clostridium ljungdahlii*, or *Clostridium ragsdalei* are not specific to that species but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the invention may also be derived from an isolate or mutant of *Clostridium autoethanogenum*, *Clostridium ljungdahlii*, or *Clostridium ragsdalei*. Isolates and mutants of *Clostridium autoethanogenum* include JA1-1 (DSM10061) (Abrini, *Arch Microbiol*, 161: 345-351, 1994), LBS1560 (DSM19630) (WO 2009/064200), and LZ1561 (DSM23693). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

"Substrate" refers to a carbon and/or energy source for the microorganism of the invention. Typically, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the invention typically converts at least a portion of the CO in the substrate to a product. In some embodiments, the substrate comprises no or substantially no (<1 mol %) CO.

The substrate may comprise some amount of H2. For example, the substrate may comprise about 1, 2, 5, 10, 15, 20, or 30 mol % H2. In some embodiments, the substrate may comprise a relatively high amount of H2, such as about 60, 70, 80, or 90 mol % H2. In further embodiments, the substrate comprises no or substantially no (<1 mol %) H2.

The substrate may comprise some amount of CO2. For example, the substrate may comprise about 1-80 or 1-30 mol % CO2. In some embodiments, the substrate may comprise less than about 20, 15, 10, or 5 mol % CO2. In another embodiment, the substrate comprises no or substantially no (<1 mol %) CO2.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the substrate may have a significant impact on the efficiency and/or cost of the reaction. For example, the presence of oxygen (02) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

The microorganism of the invention may be cultured to produce one or more products. For instance, *Clostridium autoethanogenum* produces or can be engineered to produce ethanol (WO 2007/117157), acetate (WO 2007/117157), butanol (WO 2008/115080 and WO 2012/053905), butyrate (WO 2008/115080), 2,3-butanediol (WO 2009/151342), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-TIP) (WO 2013/180581), isoprene (WO 2013/180584), fatty acids (WO 2013/191567), 2-butanol (WO 2013/185123), 1,2-propanediol (WO 2014/0369152), and 1-propanol (WO 2014/0369152). In addition to one or more target products, the microorganism of the invention may also produce ethanol, acetate, and/or 2,3-butanediol. In certain embodiments, microbial biomass itself may be considered a product.

A "native product" is a product produced by a genetically unmodified microorganism. For example, ethanol, acetate, and 2,3-butanediol are native products of *Clostridium autoethanogenum, Clostridium ljungdahlii*, and *Clostridium ragsdalei*. A "non-native product" is a product that is produced by a genetically modified microorganism, but is not produced by a genetically unmodified microorganism from which the genetically modified microorganism is derived.

"Selectivity" refers to the ratio of the production of a target product to the production of all fermentation products produced by a microorganism. The microorganism of the invention may be engineered to produce products at a certain selectivity or at a minimum selectivity. In one embodiment, a target product accounts for at least about 5%, 10%, 15%, 20%, 30%, 50%, or 75% of all fermentation products produced by the microorganism of the invention. In one embodiment, the target product accounts for at least 10% of all fermentation products produced by the microorganism of the invention, such that the microorganism of the invention has a selectivity for the target product of at least 10%. In another embodiment, the target product accounts for at least 30% of all fermentation products produced by the microorganism of the invention, such that the microorganism of the invention has a selectivity for the target product of at least 30%.

"Increasing the efficiency," "increased efficiency," and the like include, but are not limited to, increasing specific growth rate, product production rate or volume, product volume per volume of substrate consumed, or product selectivity. Efficiency may be measured relative to the performance of parental microorganism from which the microorganism of the invention is derived.

The terms "productivity" or "rate of production" is the volumetric productivity of a product. In continuous systems, the volumetric productivity is calculated as the ratio of the steady state concentration of the product and the liquid retention time. In batch systems, the volumetric productivity is calculated as the concentration and the time required to produce said concentration in a batch system. The volumetric productivity is reported as g/L/day.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time, in turn, dictates the required volume of a bioreactor, the use of pressurized systems can greatly reduce the volume of the bioreactor required, and consequently the capital cost of the fermentation equipment.

Target products may be separated or purified from a fermentation broth using any method or combination of methods known in the art, including, for example, fractional distillation, evaporation, pervaporation, gas stripping, phase separation, and extractive fermentation, including, for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor.

The use of term "acid", "acids" and the like when referring to adding an "acid" to a culture or bioreactor in accordance with the invention should be taken broadly, including any monocarboxylic and dicarboxylic acids. Reference to addition of or production of equivalent salts should be taken to include reference to the acid, or a mixture, therefore. For example reference to the term, acetate should be taken to include acetic acid and vice versa. The ratio of molecular acid to carboxylate in the fermentation broth is dependent upon the pH of the system. Exemplary acids include acetic acid, propionic acid, n-butyric acid, n-pentanoic acid, n-hexanoic acid, and benzoic acid The present invention provides methods for improving fermentation efficiency. The inventors have found that the addition of specific Amino Acids in excess of cellular requirements to a microbial culture, has a profound effect on the growth of the culture. Furthermore, the inventors have identified that this excess addition of Amino Acids enables increased production of fermentation products, especially fermentation products with high energy/ATP demands.

The present invention provides methods for improving fermentation efficiency. The inventors have found that the addition of arginine in excess of cellular requirements to a microbial culture, has a profound effect on growth of the culture. Furthermore, the inventors have identified that this excess addition of arginine enables increased production of fermentation products, especially fermentation products with high energy/ATP demands.

Without wishing to be bound by theory, it is believed that the growth increasing effect of arginine is considered to come from ATP production during arginine catabolism by the microorganism. Arginine is catabolised through either an arginine deiminase (ADI) pathway or an arginine decarboxylase pathway.

Arginine catabolism via the arginine deiminase occurs by the following mechanism:

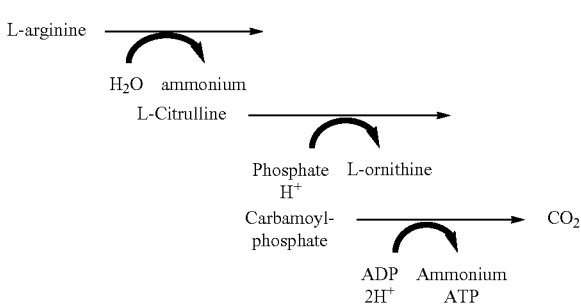

The catabolism of arginine via the ADI pathway results in the production of ammonium, $CO_2$ and ATP.

Arginine catabolism via the arginine decarboxylase pathway occurs by the following mechanism:

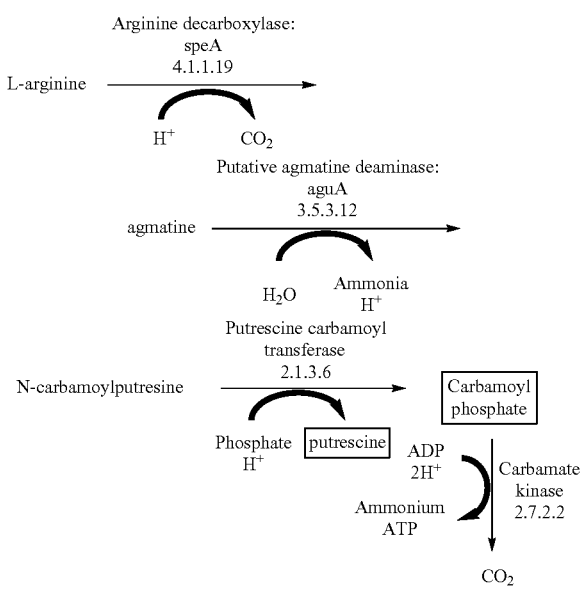

The resultant ATP production from arginine catabolism enables the increased growth profile of the microorganism.

Without wishing to be bound by theory, the inventors believe that whilst arginine catabolism provides the ATP requirement of the microorganism for growth, arginine is not utilized as a carbon source by the microorganism, rather the carbon source utilized is the carbon component in the C1 containing gas.

Processes for microbial fermentation of C1-containing gaseous substrates to produce products such as ethanol and acetate are widely known in the art. Such processes provide a means to produce commercially useful fuels from industrial waste gases comprising C1 carbon sources. These processes generally involve feeding a gaseous substrate comprising, for example, CO to a bioreactor comprising a culture of at least one acetogenic carboxydotrophic microorganisms in a liquid nutrient medium. The gaseous substrate is anaerobically fermented to produce alcohols, acids, and mixtures thereof. The liquid nutrient medium used in the bioreactor typically contains various nutrients that support growth of the at least one acetogenic carboxydotrophic microorganism and are utilised in metabolic pathways of the one or more microorganisms in order to produce alcohols. Examples of such nutrients include MgCl, CaCl, KCl, H3PO4, Fe, Ni, Zn, Mn, B, W, Se, etc.

It is also known that *Clostridium* strains, can be genetically modified to enable the production of a number of other useful products including succinate, methyl ethyl ketone (MEK), 2-butanol, propanediol, 2-propanol, isopropanol, isoprene, acetoin, iso-butanol, citramalate, butadiene, and poly lactic acid, acetone, butanol, isobutylene, 3-hydroxy propionate (3HP) and fatty acids.

Surprisingly, the inventors have found that increasing the concentration of arginine provided to the microbial culture, increased the growth profile of the microorganism, and increases the amount of ATP intensive products that can be produced by the culture.

One embodiment of the invention involves providing a liquid nutrient medium with arginine, wherein the amount of arginine provided of the liquid nutrient medium is in excess of the cellular requirements of the C1-fixing microorganism. Providing arginine in excess of the cellular requirements of the C1-fixing microorganism has the effect of increasing the specific growth rate of the microbial culture. In some embodiments the specific growth rate of the C1-fixing microorganism in increased by at least 10%, or by at least 20%, or by at least 30%, or by at least 40%, or by at least 50%, or by at least 60%, or by at least 70% compared to microorganism without an excess of arginine.

The cellular requirement of arginine by a microorganism can be estimated by the determination of the amino acid composition of biomass after biomass hydrolysis and amino acid analysis.

It has been demonstrated that by increasing the concentration of arginine in the liquid nutrient media from equaling the cellular requirement to 1000 times (or more) above the requirement for biomass synthesis, the doubling time of the microorganism decreased. In certain embodiments, the doubling time of the culture provided with an excess of arginine decreased to 3.5 h compared to a doubling time of 7.3 h in a culture without the excess of arginine. Without wishing to be bound by theory, the inventors also believe that by increasing the concentration of arginine from 2 to 80 times (or more) above cellular requirement increases the productivity rate of ATP-intensive fermentation products. In certain embodiments arginine is provided to the culture at from 2 to 1000 or from 2 to 800 or from 2 to 500 or from 2 to 100 or from 2 to 50 or from 2 to 10 or from 50 to 1000, or from 50 to 800, or from 50 to 600, or from 50 to 500, or from 50 to 300 or from 50 to 200, or from 50 to 100 or from 100 to 1000 or from 100 to 800 or from 100 to 600 or from 100 to 500 or from 100 to 300 or from 100 to 200 times the requirement for synthesis of biomass.

In terms of actual concentration, a broad embodiment of the invention is one in which the arginine concentration in the liquid nutrient medium is from 20 mg/L to about 20 g/L. In particular embodiments the concentration of arginine is maintained at an amount of at least 20 mg/L, or at least 100 mg/L or at least 300 mg/L or at least 500 mg/L, or at least 1 g/L or at least 2 g/l, or at least 3 g/l, or at least 4 g/L or at least 5 g/L or at least 10 g/L, or at least 20 g/L. In certain embodiments, the concentration of arginine is maintained at between 20 mg/L to about 20 g/l. or between 100 mg/L to 20 g/L, or between 500 mg/l to 20 g/L, or between 500 mg/L to 10 g/L, or between 1 g/L to 10 g/L or between 5 g/L to 10 g/L, or between 5 g/L to 20 g/L. In certain embodiment's arginine is provided to the culture such that arginine consumption by the culture was at least 20 mg arginine per gram of dry cell weight or at least 100 mg arginine per gram of dry cell weight, or at least 1 grams arginine per gram of dry cell weight, or at least 5 grams arginine per gram of dry cell weight, or at least 10 grams arginine per gram of dry cell weight. In certain embodiments, arginine is provided to the culture such that arginine consumption by the culture is between 20 mg to 20 grams per gram of dry cell weight, or between 100 mg and 20 grams per gram of dry cell weight, or between 1 gram and 10 grams per gram of dry cell weight.

In certain embodiments at least 0.012 g arginine is consumed by the culture to produce 1 g biomass. In certain embodiments, the cellular requirement of arginine for biomass synthesis is between 0.012 g per gram biomass to about 24 g per gram biomass. In certain embodiments the arginine requirement for biomass synthesis is at least 0.012 g per gram biomass, or at least 0.024 g per gram biomass, to about 0.048 g per gram biomass, or least 0.120 g per gram biomass, or at least 0.24 g per gram biomass, or at least 0.48 g per gram biomass, or at least 1.2 g per gram biomass, or at least 2.4 g per gram biomass, or at least 4.8 g per gram biomass, or at least 12 g per gram biomass.

In some embodiments of the present invention increasing the concentration of arginine in the liquid nutrient media from 2 to 80 times (or more) above cellular requirement increases the doubling time of the microorganism by at least 10%, or by at least 20%, or by at least 30%, or by at least 40%, or by at least 50%, or by at least 60%, or by at least 70%.

When arginine was increased above the cellular requirement of *Clostridium autoethanogenum* the production of acetate by the microorganism was reduced. Without wishing to be bound by theory, the inventors believe that the ability of *Clostridium autoethanogenum* to utilize arginine to produce ATP for growth negates the need of the microorganism to produce acetate for acquiring ATP when arginine is supplied.

All acetogenic microorganisms are described to produce acetate (Drake, Acetogenic Prokaryotes, In The Prokaryotes, 3rd edition, pages 354-420, New York, NY, Springer, 2006) as the production of acetate provides the microorganism with an option to directly generate ATP from substrate level phosphorylation via Pta (phosphotransacetylase) and Ack (phosphotransacetylase-acetate kinase). Particularly on a commercial scale, it is not desirable for microorganisms to produce acetate (or other organic acids required for the CoA transferase reaction) as by-product, since acetate diverts carbon away from target products and thus affects the efficiency and yield of target products. Additionally, acetate may be toxic to microorganisms and/or may serve as a substrate for the growth of contaminating microorganisms. Furthermore, the presence of acetate makes it more difficult to recover and separate target products and to control fermentation conditions to favour the production of target products.

The provision of arginine in excess of cellular requirements to a *Clostridium autoethanogenum* culture results in greatly reduced acetate production when compared to a culture where arginine is not provided in excess of cellular requirements. Further, the inventors have demonstrated that acetate production increases in a culture, once the arginine source has been fully depleted. In one embodiment, the provision of excess arginine to the microbial culture reduces acetate production by 20% or by 30% or by 40% or by 50%, or by 60%, or by 70% or by 80%.

It has been demonstrated by the inventors that Arginine is stoichiometrically converted to ornithine, implicating the arginine deiminase pathway as the mechanism for the catabolism of arginine. This pathway would convert arginine into ornithine, ammonium, ATP, and $CO_2$. Enhanced growth would be facilitated by the supply of ATP and ammonium from arginine degradation. In one embodiment, the present invention provides a method for improving the sustainability of a fermentation process, wherein arginine is provided to the microbial culture in the absence of an alternative nitrogen source.

It is well known in the art that nitrogen is required by the microorganism for growth. Nitrogen is typically provided to the culture in the form of ammonium salt or ammonium hydroxide. Ammonia is typically produced by the Haber process which is characterized by the following reaction:

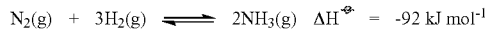

$$N_2(g) + 3H_2(g) \rightleftharpoons 2NH_3(g) \quad \Delta H^{\ominus} = -92 \text{ kJ mol}^{-1}$$

Currently, ammonia is produced primarily from natural gas and coal. In a typical ammonia production process from natural gas, hydrogen is sourced from natural gas and nitrogen is derived from the atmosphere. Natural gas produces greenhouse gases, so whilst ammonia itself does not produce greenhouse gases, the production of ammonia does. It is desirable to find and utilize sources of ammonia that are completely renewable. [http://www.agmrc.org/renewable_energy/renewable_energy/ammonia-as-a-transportation-fuel/]. Costs for Ammonium Hydroxide (28.0 to 30.0 w/w) are in the range of US$9600 per 1000 Kilograms.

Arginine (L-Arginine) was first isolated from lupine seedling extract in 1886. It was later identified to be widely distributed in foods and feeds. Arginine can be produced by a variety of methods including protein hydrolysis, chemical synthesis, and microbiological synthesis. Most L-arginine is produced by direct fermentation using renewable carbon sources. [jn.nutrition.org/content/134/10/2854S.full]

The identified pathway of example 3 allows conversion of 1 mol of arginine to 3 mol of ammonia. Thus arginine can provide an alternative nitrogen source for the bacteria, providing ammonia directly in the metabolism, while still providing advantages described above. Since 1 molecule of arginine can be broken down to 3 molecules of ammonia, lower quantities required lead to significant cost savings from cheaper price of arginine (99% food grade arginine costs around ~US$17-18,000/1000 kg while 30% industrial grade ammonia is ~US$10-11,000/1000 kg from Sigma Aldrich or Fisher) and reduced handling. In addition, arginine can be derived sustainable from biological sources, for example by fermentation (T. Utagawa, J. Nutr., 2004, 134, 2854S-2857).

The Arginine deiminase pathway proceeds via three enzymatic steps, catalysed by arginine deiminase (EC 3.5.3.6), a carbomyltransferase (ornithine carbomyltransferase, putrescine carbomyltransferase) (EC 2.1.3.3) and a carbamate kinase (EC 2.7.2.2). Respective enzymes have been identified in the genome of *C. autoethanogenum*.

Another aspect of the invention further provides a genetically engineered C1-fixing bacterium comprising an improved arginine deiminase pathway. In one embodiment the invention provides a genetically engineered C1-fixing bacterium comprising one or more enzymes selected from the group consisting of: arginine deiminase (EC 3.5.3.6), carbomyltransferase (ornithine carbomyltransferase, putrescine carbomyltransferase) (EC 2.1.3.3), and carbamate kinase (EC 2.7.2.2), wherein each enzyme is an overexpressed endogenous enzyme, a mutated endogenous enzyme of an exogenous enzyme. In particular embodiments, the C1-fixing bacterium is a *Clostridium* bacterium. In particular embodiments, the bacterium is *Clostridium autoethanogenum*.

Whilst not wishing to be bound by theory, the inventors believe that to increase performance, in particular, if accumulation of intermediates as citruline is observed, of the pathway, respective genes can be overexpressed or genes from other sources can be introduced and heterologously expressed by someone skilled in the art using methods described before (WO2012/053905, WO2012/115527, WO2013-180584).

The invention further provides a method for producing at least one product from a substrate, the method comprising culturing a genetically engineered C1-fixing bacterium comprising one or more enzymes selected from the group consisting of: arginine deiminase (EC 3.5.3.6), carbomyltransferase (ornithine carbomyltransferase, putrescine carbomyltransferase) (EC 2.1.3.3), and carbamate kinase (EC 2.7.2.2), wherein each enzyme is an overexpressed endogenous enzyme, a mutated endogenous enzyme of an exogenous enzyme.

Another aspect of the invention further provides a genetically engineered C1-fixing bacterium comprising one or more enzymes selected from the group consisting of ornithine racemase (EC 5.1.1.12), ornithine aminomutase (EC 5.4.3.5), 2,4-diaminopentanoate dehydrogenase (EC 1.4.1.12) and 2-amino-4-oxopentanoate thiolase. Without wishing to be bound by theory, the inventors believe that respective genes can be overexpressed or genes from other sources can be introduced and heterologously expressed by someone skilled in the art using methods described before (WO2012/053905, WO2012/115527, and WO2013-180584). The organism may also be adapted and evolved to utilize ornithine more effectively if it is adapted for growth on arginine over time. This is supported by the observation of an accumulation of ornithine.

The inventors have identified an arginine repressor that controls gene expression by binding to a palindromic operator sequence that is located approximately 45 bp upstream of the arginine deiminase start codon. Addition of arginine causes the repressor to unbind the operator sequence, allowing transcription of the genes down-stream of the operator sequence. In one aspect of the invention, there is provided a genetically engineered recombinant bacterium comprising at least one heterologous gene, said heterologous gene being provided downstream of an argR-binding operator sequence, wherein gene expression of the at least one heterologous gene can be activated by addition of arginine.

The invention further provides a method for producing at least one product, the method comprising providing a carbon source to a culture containing a genetically engineered bacterium comprising at least one heterologous gene, said heterologous gene being provided downstream of an argR-binding operator sequence, providing the culture with arginine, and fermenting the culture. In certain embodiments, the at least one heterologous gene is a heterologous gene in the biosynthesis pathway of the product.

In one example the heterologous genes may encode for a metabolic pathway that requires ATP for synthesis of the product. For example, the mevalonate pathway is a heterologous pathway that converts acetyl-CoA to isopentenyl-diphosphate at a cost of 3 mol ATP per mol isopentenyl-diphosphate. Using the method described, expression of the heterologous mevalonate pathway could be activated by addition of arginine, which would also provide ATP for the mevalonate pathway through degradation of arginine via the arginine deiminase pathway.

In another aspect, arginine can be utilized via an arginine decarboxylation pathway. Without wishing to be bound by theory, the inventors believe that arginine can be decarboxylated to agmatine and CO2 by the enzyme arginine decarboxylase. Agmatine can subsequently be converted to N-carbamoyl putrescine by the enzyme agmatine deiminase, also yielding ammonium. N-carbamoyl-putrescine plus phosphate can be converted to putrescine plus carbamoyl-phosphate by putrescine carbamoyl transferase. Carbamoyl phosphate plus ADP is converted to ammonium+ATP+CO2 by carbamate kinase via the same mechanism as in the arginine deiminase pathway. The net yield of ammonium and ATP is the same as the arginine deiminase pathway but with two different intermediates (agmatine and N-carbamoyl putrescine) and a different by-product (putrescine). Putrescince is a by-product of greater value than either ornithine or arginine and can be used as a feedstock for the production of a variety of polymers including nylon-4,6 (Qian et al. 2009, Biotechnol. Bioeng. 104, pp. 651-662) and polyurethane.

Figure 23:
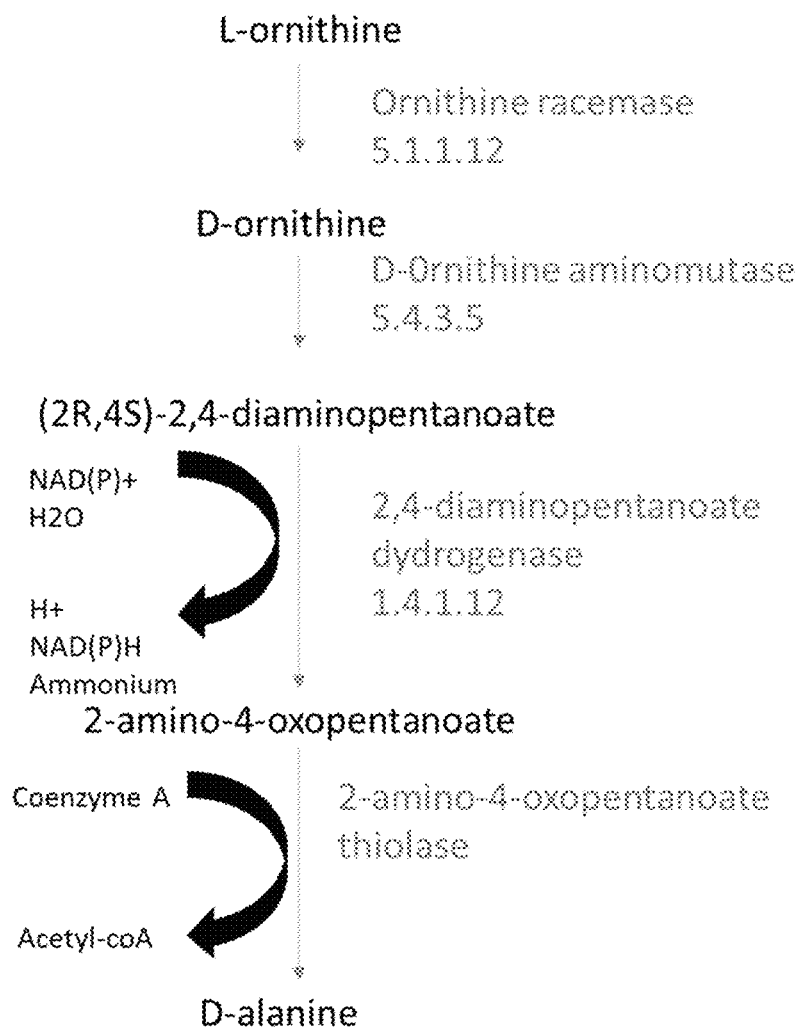
FIG. 23 shows enzymes required for ornithine consumption in *Clostridium sticklandii*.

In another aspect, the bacterium is modified to overexpress one or more endogenous genes, express one more mutated endogenous genes, or heterologously express one or more exogenous genes, encoding enzymes selected from the group consisting of ornithine racemase, ornithine aminomutase, subunit beta (OraE), ornithine aminomutase, subunit alpha (OraS), 2,4-diaminopentanoate dehydrogenase, 2,4-diaminopentanoate dehydrogenase, 2-amino-4-oxopentanoate thiolase, beta subunit, 2-amino-4-oxopentanoate thiolase, alpha subunit, and functionally equivalent variants thereof. Alternatively, the bacterium can be modified to express one or more exogenous genes selected from the group consisting of ornithine racemase, ornithine aminomutase, subunit beta (OraE), ornithine aminomutase, subunit alpha (OraS), 2,4-diaminopentanoate dehydrogenase, 2,4-diaminopentanoate dehydrogenase, 2-amino-4-oxopentanoate thiolase, beta subunit, and 2-amino-4-oxopentanoate thiolase, alpha subunit. In preferred embodiments, the endogenous genes are derived from *Clostridium sticklandii* (FIG. 23). Without wishing to be bound by theory, the inventors consider that over expression of these genes results will result in increased performance in the arginine deiminase pathway, particularly when ornithine accumulation is observed in the parent strain. Alternatively, it is considered that the bacterium may be adapted and evolved to utilize ornithine more effectively. In certain embodiments, the bacterium is selected for growth on arginine.

In another aspect, the bacterium comprises one or more genetic modification which disrupts an arginine:ornithine transporter. In one embodiment, the genetic modification disrupts the expression of CAETHG_3023 and CAETHG 3024 (Genbank GeneID: 17336441 and 17336442; Genbank protein accession number: YP_008700482.1 and YP_008700483.1). Preferably genetic modification is a gene knockout mutation. Knock-out of the arginine: ornithine transporter results in a decrease of ornithine being exported from the bacterial cell, and enables ornithine metabolism by the cell. Additionally, the bacterium can be modified to express an alternative arginine transporter to import arginine without export of ornithine. In alternative embodiments, the bacterium can be modified to express an ornithine importer to enable recapture of excreted ornithine. Each of these approaches will increase the ability of the bacterium to metabolize ornithine.

Example 1 demonstrates the production of alanine from arginine by *C. autoethanogenum*. In one aspect, the invention provides a method for the production of one or more products derived from alanine, the products derived from alanine including 3-hydroxypropionate (3-HP) or acrylic acid. Acrylic acid is an important commodity with uses in in polymeric flocculants, dispersants, coatings, paints, adhesives, and binders for leather, paper, and textile with an estimated global demand of 5 million tonnes in 2014. 3-HP is a platform for acrylic acid, methylacrylic acid, acrylamide or 1,3-propanediol.

In one aspect, the invention provides a genetically engineered C1-fixing bacterium comprising at least one heterologous enzyme selected from the group consisting of: enzymes for converting alanine to malonyl-semialdehyde and 3-HP, enzymes for converting alanine to alanyl-CoA, enzymes for converting 3-HP to acrylyl-CoA, enzymes for converting alanyl-CoA to acrylyl-CoA, and enzymes for converting to acrylyl-CoA to acrylate.

In particular embodiments, the C1 fixing microorganism is an acetogenic carboxydotrophic microorganism. Examples of suitable C1-fixing microorganisms include *Clostridium, Moorella, Oxobacter, Peptostreptococcus, Acetobacterium, Eubacterium*, or *Butyribacterium*. In various embodiments, the microorganism is selected from the group of microorganisms identified in Table 5.

EXAMPLES

The following examples further illustrate the invention but, of course, should not be construed to limit its scope in any way.

TABLE 1

PETC-MES media without yeast extract

| Component | Amount per 1 L of medium |
| --- | --- |
| NH$_4$Cl | 1 g |
| KCl | 0.1 g |
| MgSO$_4$•7H$_2$O | 0.2 g |
| KH$_2$PO$_4$ | 0.2 g |
| CaCl$_2$ | 0.02 g |
| 2-(N-morpholino)ethanesulfonic acid (MES) | 20 g |
| Sodium acetate | 0.1 g |
| Fe(SO$_4$) × 7H$_2$O | 0.05 g |
| Nitrilotriacetic Acid | 0.05 g |
| Resazurin (2 g/L stock) | 0.5 ml |
| Trace metal solution (see below) | 10 ml |
| Wolfe's vitamin solution (see below) | 10 ml |

TABLE 1-continued

PETC-MES media without yeast extract

| | |
|---|---|
| Reducing agent solution 1 (see below) | 5 mL |
| Reducing agent solution 2 (see below) | 5 mL |
| pH 5.6 | Adjusted with 4N NaOH |

| Trace metal solution | per 1000 mL of stock |
|---|---|
| Nitrilotriacetic Acid | 2 g |
| $MnSO_4 \cdot H_2O$ | 1 g |
| $Fe(SO_4) \times 7H_2O$ | 0.56 g |
| $CoCl_2 \cdot 6H_2O$ | 0.2 g |
| $ZnSO_4 \cdot 7H_2O$ | 0.2 g |
| $CuCl_2 \cdot 2H_2O$ | 0.02 g |
| $NaMoO_4 \cdot 2H_2O$ | 0.02 g |
| $Na_2SeO_3 \times 5H_2O$ | 0.03 g |
| $NiCl_2 \cdot 6H_2O$ | 0.02 g |
| $Na_2WO_4 \cdot 2H_2O$ | 0.02 g |
| pH 7.6 | Adjusted with 5M KOH |

| Wolfe's vitamin solution | per 1000 mL of Stock |
|---|---|
| Biotin | 2 mg |
| Folic acid | 2 mg |
| Pyridoxine hydrochloride | 10 mg |
| Thiamine•HCl | 5 mg |
| Riboflavin | 5 mg |
| Nicotinic acid | 5 mg |
| Calcium D-(+)-pantothenate | 5 mg |
| Vitamin $B_{12}$ | 0.1 mg |
| 4-Aminobenzoic acid | 5 mg |
| Thioctic acid | 5 mg |

| Reducing agent 1 (storage anaerobic, dark) | per 100 mL of Stock |
|---|---|
| L-Cysteine-HCl | 4 g |

| Reducing agent 2 (storage anaerobic, dark) | per 100 mL of Stock |
|---|---|
| NaOH | 0.9 g (dissolve first) |
| L-Cysteine-HCl | 4 g (dissolve after NaOH) |
| $Na_2S * 9H_2O$ | 4 g (dissolve after cysteine) |

TABLE 2

Amino acid formulations with final concentrations in g/L

| Amino acid | 20AA | 8AA | 14AA | 12AA | 4AA | Arginine |
|---|---|---|---|---|---|---|
| Tryptophan | 0.004 | | 0.017 | | | |
| Tyrosine | 0.069 | | | | | |
| Threonine | 0.022 | 0.088 | 0.088 | 0.176 | | |
| Valine | 0.062 | 0.246 | 0.246 | 0.246 | | |
| Proline | 0.024 | | | | | |
| Alanine | 0.029 | | | | | |
| Arginine | 0.011 | 0.044 | 0.044 | 0.881 | 0.881 | 5.000 |
| Aspartic acid | 0.010 | 0.076 | 0.076 | 0.761 | 0.761 | |
| Asparagine | 0.009 | | | | | |
| Cysteine | 0.067 | | 0.453 | 0.905 | | |
| Histidine | 0.011 | 0.042 | 0.042 | 0.849 | 0.849 | |
| Isoleucine | 0.026 | | 0.105 | 0.105 | | |
| Glutamic acid | 0.009 | 0.034 | 0.034 | 0.690 | 0.690 | |
| Glutamine | 0.009 | | 0.035 | | | |
| Glycine | 0.033 | | | | | |

Example 1

Identification of Preferred Amino Acids of Acetogen *C. autoethanogenum* and Enhanced Growth with Arginine Supplementation This example demonstrates that arginine, histidine, aspartate, and glutamate are distinctively preferred over other amino acids and consumed at >80-fold higher yields than needed for biomass synthesis by acetogen *C. autoethanogenum* DSM10061 and supplementation of arginine into defined medium enables *C. autoethanogenum* to grow with tD~3 h, which is ~3-fold faster compared to supplementation with yeast extract (YE).

*Clostridium autoethanogenum* DSM 10061 was sourced from DSMZ (The German Collection of Microorganisms and Cell Cultures, Inhoffenstraße 7 B, 38124 Braunschweig, Germany).

YE-free PETC-MES media was supplemented with various amino acid formulations—20AA, 7AA, 8AA, 14AA, 12AA, 4AA and Arginine (Table 2)—to identify if any amino acids are supporting growth. Solutions were filter sterilized and made anoxic by sparging N2.

First, a 20AA medium was designed based on the biomass amino acid composition of *Clostridium acetobutylicum* (Lee et al. 2008) with final amino acid concentrations theoretically supporting production of 1 gDCW/L of biomass.

Growth studies were carried out in batch cultivations in a volume of 50 mL media in 125 mL serum bottles with nitrogen in the headspace under shaking (unless otherwise noted) at 37° C. Optical density (OD) was measured at 600 nm with the reading ~0.5 outside the anaerobic chamber against fully oxidized medium as reference.

Organic acids, fructose and amino acids analyzed by HPLC. Analysis Organic acids, carbohydrates, and alcohols were quantified by ion-exclusion chromatography using an Agilent 1200 HPLC system and an Agilent Hiplex H column (300×7.7 mm, PL1170-6830) with guard column (Security-Guard Carbo-H, Phenomenex PN: AJO-4490). In general, sugars and alcohols were monitored using a refractive index detector (Agilent RID, G1362A) set on positive polarity and optical unit temperature of 40° C., while organic acids were monitored at 210 nm (Agilent MWD, G1365B) and/or with refractive index detector. 30 μL of sample was injected onto the column using an autosampler (Agilent HiP-ALS, G1367B) and column temperature kept at 65° C. using a thermostatted column compartment (Agilent TCC, G1316A). Analytes were eluted isocratically with 4 mM H2SO4 at 0.6 mL/min for 26 min. Fructose, sucrose, and glucose were analysed separately at a column temperature of 15° C. and by using high purity water (18.2 MΩ·cm) as the mobile phase and eluted isocratically at 0.4 mL/min for 21 min. Chromatograms were integrated using ChemStation (Dietmair S, Timmins N E, Gray P P, Nielsen L K, Kromer J O: Towards quantitative metabolomics of mammalian cells: development of a metabolite extraction protocol. Analytical biochemistry 2010, 404:155-164). Amino acids were measured and quantified as described previously (R. B. McQualter, C. Bellasio, L. K. Gebbie, L. A. Petrasovits, R. W. Palfreyman, M. P. Hodson, M. R. Plan, D. M. Blackman, S. M. Brumbley and L. K. Nielsen, *Plant Biotechnol. J.*, 2015).

Though the maximum OD reached on 20AA medium was slightly lower (~20%) than on yeast extract, equally fast growth was observed (doubling time tD=~9 h; growth rate p=0.077) in the beginning of sampling (FIG. 1).

Figure 2:
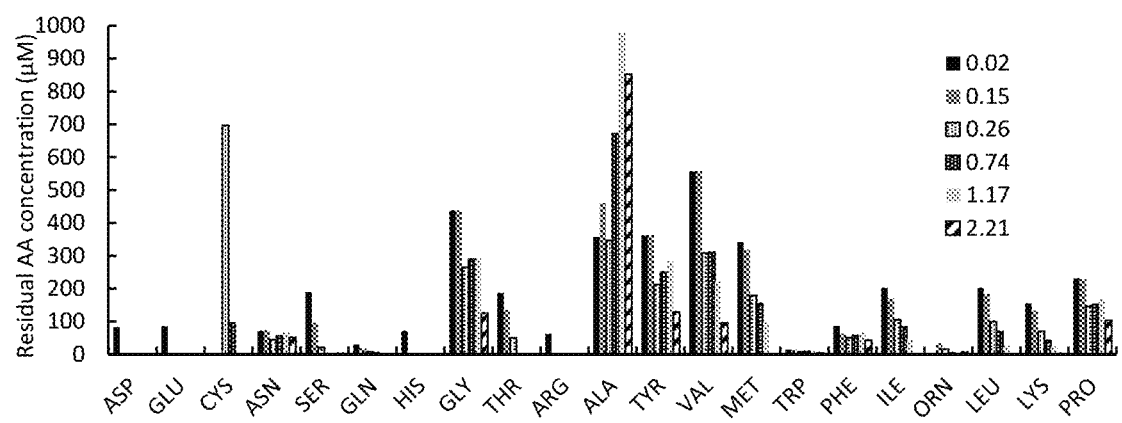
FIG. 2 is a graph showing amino acid consumption and production data for *C. autoethanogenum* DSM10061 growing on 20AA medium. Label denotes OD at sampling; cysteine measurement for first two samples was out of calibration range.

AA analysis surprisingly showed preferred and rapid utilization of AAs aspartate, glutamate, serine, histidine and threonine (FIG. 2). Arginine was rapidly exhausted from the media. More importantly, serine and threonine were consumed at >6-fold and aspartate, glutamate, histidine and arginine>20-fold higher yields than needed for the production of biomass indicating their utilization for other purposes than incorporation into biomass. Notably, accumulation of alanine, instead of its consumption, was observed on both media during growth. Based on these results, subsequent media with 2 and 4-fold higher concentrations were designed to obtain a more minimal medium, faster growth, and higher OD: 14AA medium by omitting six AAs not consumed at all or consumed slowly and 8AA medium by reducing amino acids further.

Figure 3:
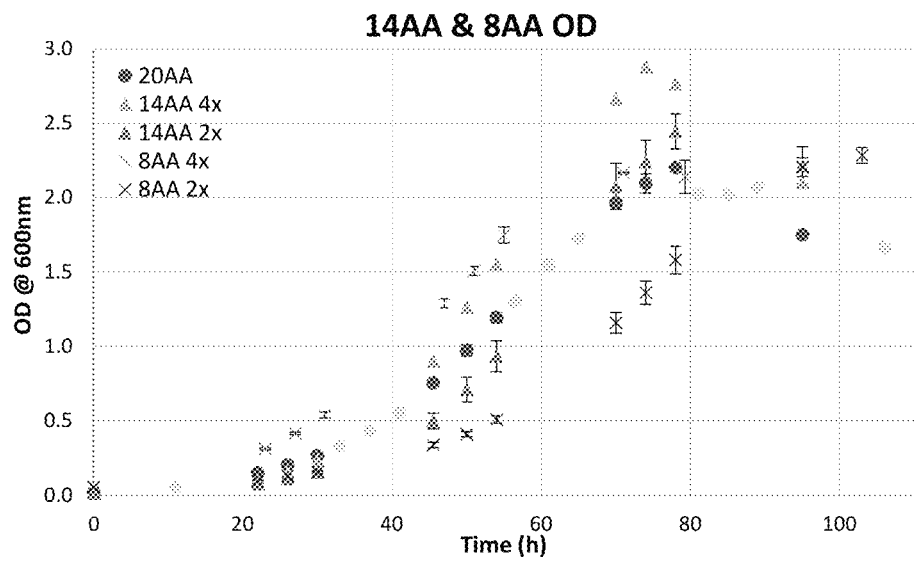
FIG. 3 is a graph showing growth for *C. autoethanogenum* DSM10061 on 14AA and 8AA media together with comparison to 20AA medium. Error bars represent standard deviation between duplicate cultures. 4× and 2× mean 4-fold and 2-fold higher AA concentrations compared to 20AA medium, respectively.
Figure 4:
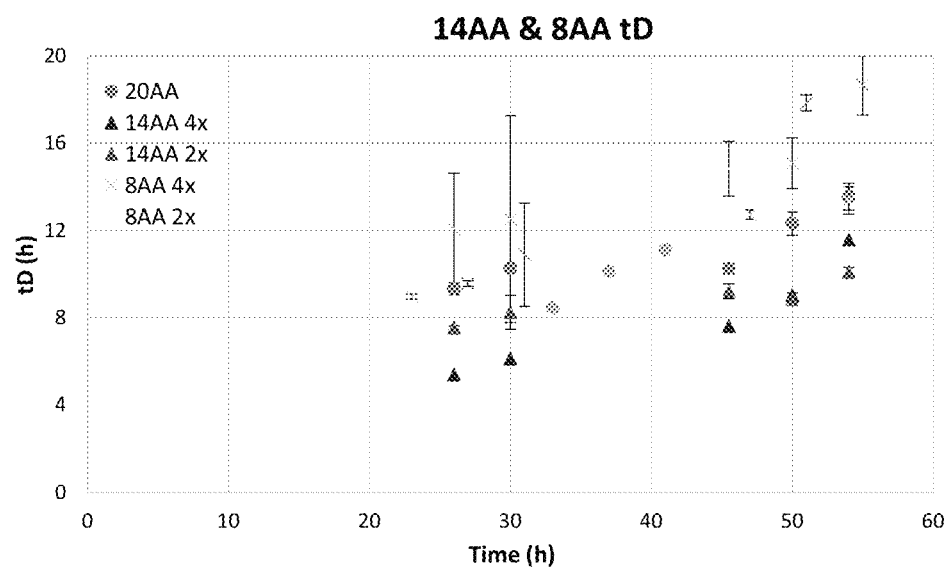
FIG. 4 is a graph showing doubling time tD for *C. autoethanogenum* DSM10061 for 14AA and 8AA media compared to the 20AA medium. tD, doubling time; Error bars represent standard deviation between duplicate cultures. 4× and 2× mean 4-fold and 2-fold higher AA concentrations compared to 20AA medium, respectively.

In 14AA medium with 4× increased AA concentrations, higher maximum OD was achieved compared to growth on yeast extract (FIG. 3). Importantly, the maximum OD achieved on the 8AA medium matched that of the 20AA medium showing that a more minimal AA formulation can support good growth. Increasing the concentrations of AAs had a positive effect on doubling time: faster and equally fast growth was achieved on 14AA and 8AA media, respectively, compared to yeast extract and the 20AA medium (FIG. 4).

Figure 5:
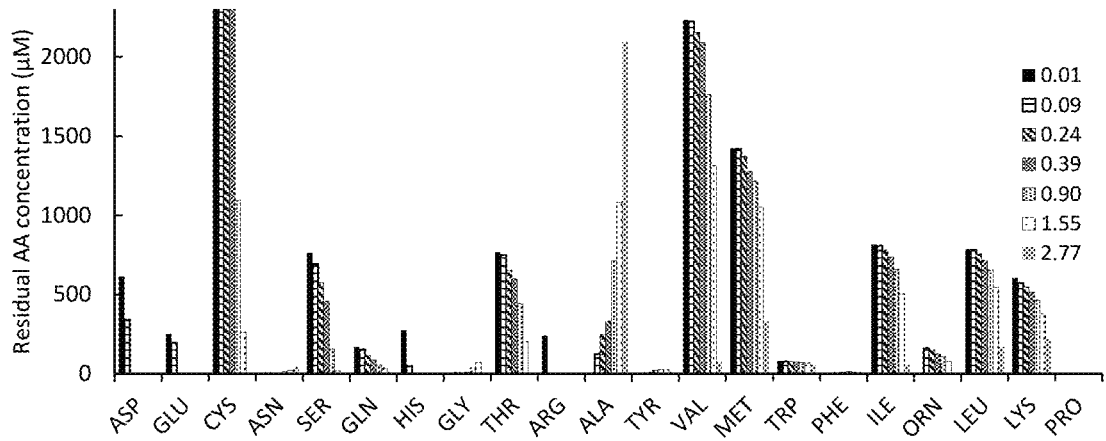
FIG. 5 is a graph showing amino acid consumption and production data of *C. autoethanogenum* DSM10061 in 14AA 4× medium. 4× means 4-fold higher AA concentrations compared to 20AA medium. Label denotes OD at sampling.
Figure 6:
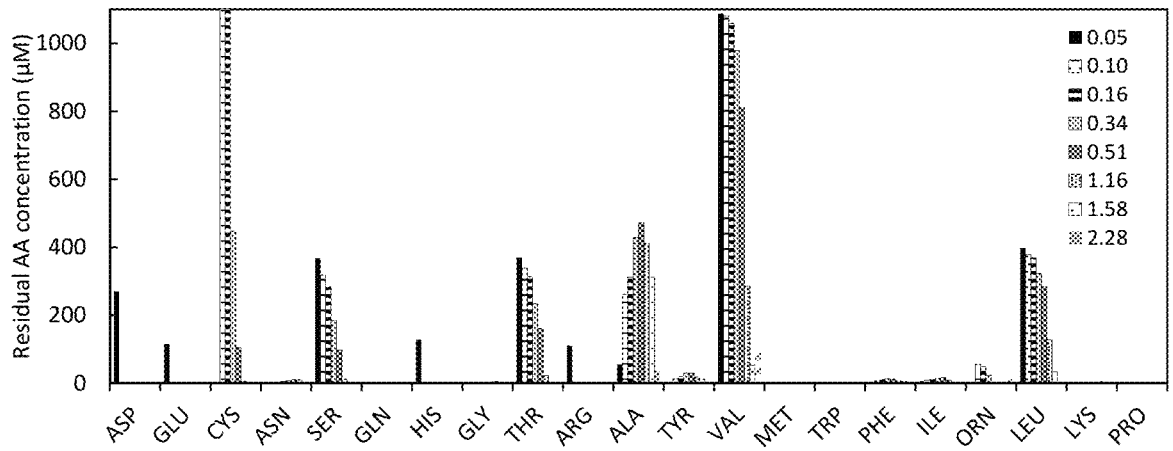
FIG. 6 is a graph showing amino acid consumption and production data of *C. autoethanogenum* DSM10061 in 8AA 2× medium. 2× means 2-fold higher AA concentrations compared to 20AA medium. Label denotes OD at sampling; cysteine measurement for the first sample was out of calibration range.

AA analysis confirmed the previous findings and further highlighted the importance of the AAs aspartate, glutamate, histidine and arginine (FIG. 5 & FIG. 6). Notably, arginine was the most preferred amino acid as it was already depleted by OD=0.24. Among the other AAs, serine and threonine were utilised faster. Again, significant accumulation of alanine was observed on both media. Interestingly, ornithine was also produced. Aspartate, glutamate, histidine and arginine were consumed >10-fold higher yields than needed for the production of biomass, indicating their use for energy generation.

Based on these results, two subsequent media were designed to obtain faster growth: 12AA medium by omitting glutamine and tryptophan from the 14AA medium and increasing the concentrations of serine, threonine and cysteine 8-fold and a media consisting only of the 4 identified AAs aspartate, glutamate, histidine and arginine to 80-fold compared to 20AA medium (2- and 20-fold compared to 14AA medium); 4AA medium containing only the "4 top AAs" aspartate, glutamate, histidine and arginine at 80-fold higher concentrations compared to 20AA medium.

Figure 7:
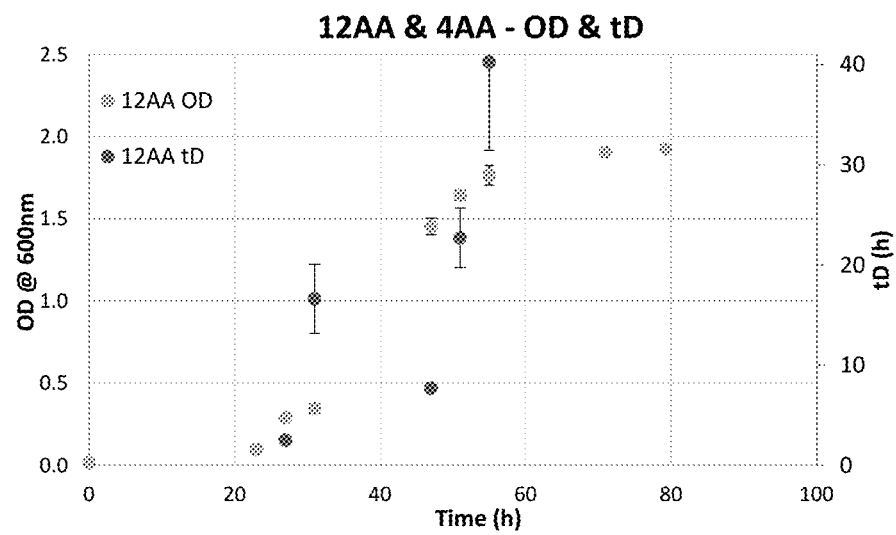
FIG. 7 is a graph showing growth data for of *C. autoethanogenum* DSM10061 in 12AA and 4AA media. Error bars represent standard deviation between duplicate cultures.

The design of the 4AA medium supported a higher maximum OD than the 12AA medium and matched the maximum OD obtained on yeast extract and 20AA medium (FIG. 7). In both 4AA and 12AA media, fast growth—tD~2.5 h—was measured up to OD~0.3, after which growth slowed down. It is important to note that the achieved tD~2.5 h is ~4-fold faster compared to supplementation with 1 g/L yeast extract as commonly used.

Figure 8:
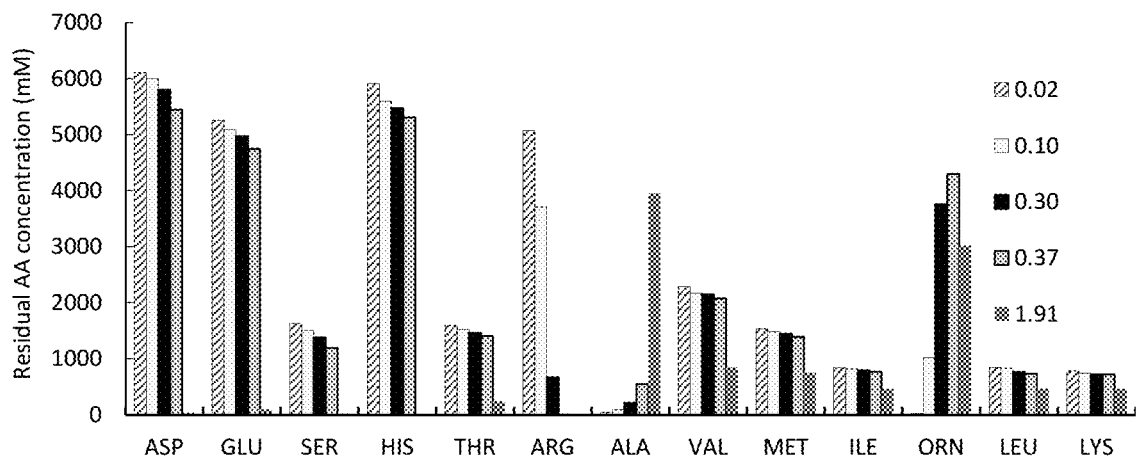
FIG. 8 is a graph showing amino acid consumption and production data for *C. autoethanogenum* DSM10061 in 12AA medium. Label denotes OD at sampling.

The fast initial growth followed by a slowdown can be explained by the depletion of arginine. From the 12AA medium AA analysis data, one can see that arginine is the preferred AA and it was completely exhausted by OD=0.37 (FIG. 8). This data also indicates that arginine strongly boosts growth together with glutamate, aspartate and histidine by supporting tD~2.5 h as was measured between ODs 0.1-0.3 while growth slowed down after arginine was depleted between ODs 0.3-0.37. Simultaneous accumulation of ornithine was observed. Again significant accumulation of alanine was detected.

Figure 9:
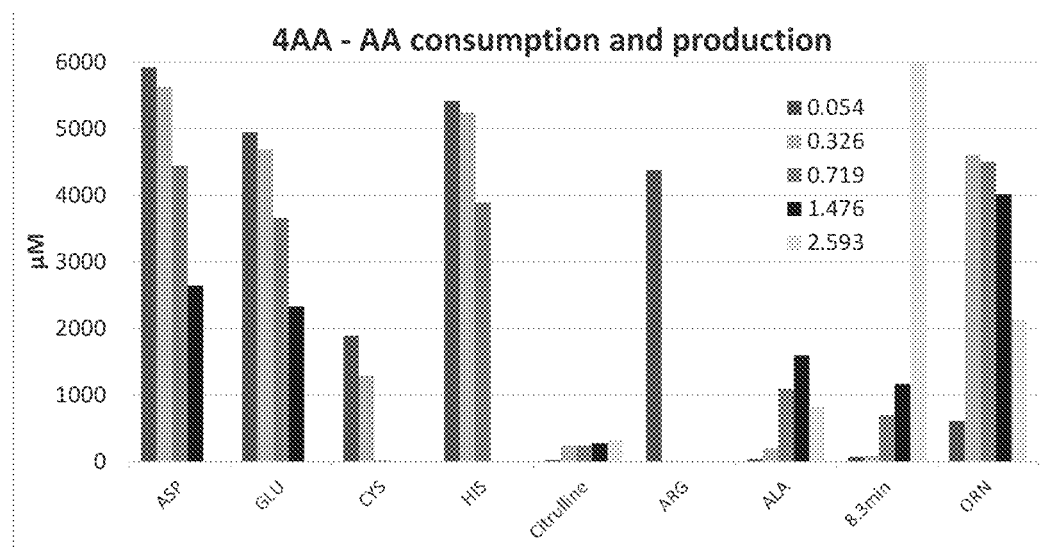
FIG. 9 is a graph showing amino acid consumption and production data for *C. autoethanogenum* DSM10061 in 4AA medium. Label denotes OD at sampling; μM unit not applicable to the 8.3 min peak.

The slowdown of growth after arginine depletion is also evident in the 4AA medium (FIG. 9). Beside ornithine but also citrulline accumulation was detected during arginine catabolism. In addition to accumulation of alanine, for the first time small amounts (~0.3 mM) of lysine and valine accumulated while also an unknown peak (8.3 min retention time) showed increasing peak areas.

Figure 10:
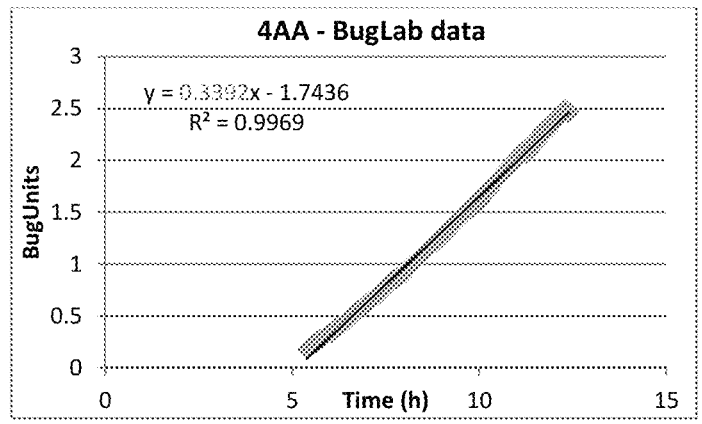
FIG. 10 is a graph showing growth data for *C. autoethanogenum* DSM10061 in 4AA medium using BugLab. BugUnits, ln of raw data. Specific growth rate 0.34 h-1 is tD~2 h.

As the initial fast growth was unexpected, only a couple of samples could be used for calculating tD. Thus, a BugLab biomass monitoring device was attached to a serum bottle on 4AA medium to continuously monitor the increase of biomass before arginine is depleted from the medium. This experiment confirmed the fast growth on 4AAs before arginine depletion as tD was calculated to be ~2 h (FIG. 10).

Figure 11:
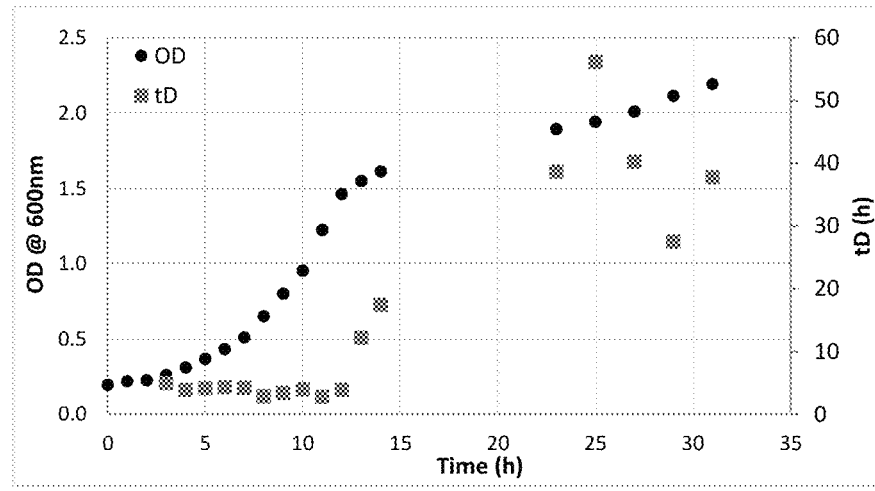
FIG. 11 is a graph showing growth data for *C. autoethanogenum* DSM10061 in YE-free PETC-MES media with 5 g arginine/L+5 g fructose/L.

Even arginine supplementation alone resulted in very good growth with equally high maximum OD as on 4AA medium and yeast extract. Growth of $C.$ $autoethanogenum$ DSM10061 in YE-free PETC-MES media with 5 g arginine/L+5 g fructose/L resulted in rapid initial growth early on (tD approx. 3 h) followed by slower growth in second stage after arginine depletion (tD~40 h) (FIG. 11).

Figure 12:
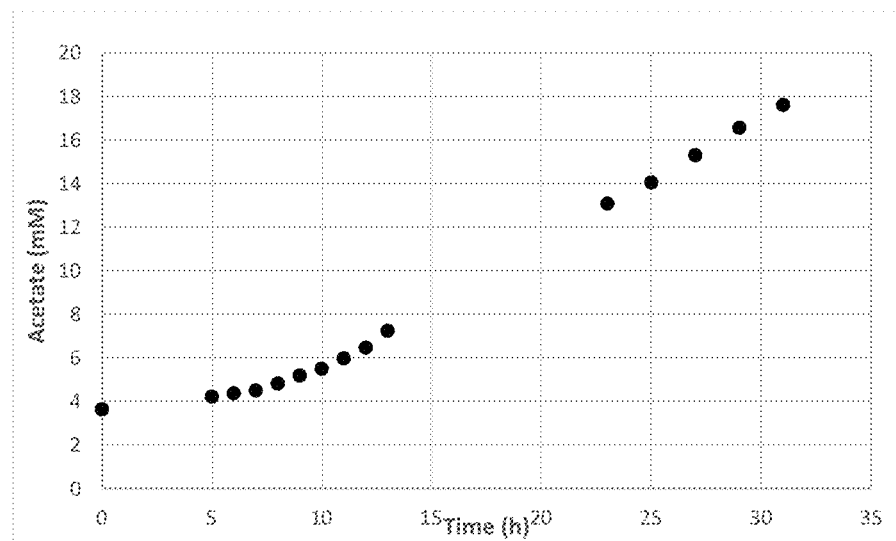
FIG. 12 is a graph showing acetate production data for *C. autoethanogenum* DSM10061 in YE-free PETC-MES media with 5 g arginine/L+5 g fructose/L.

Surprisingly during initial rapid growth phase, little acetate is produced. Acetate production is again linked to growth in the second, slower growth phase (FIG. 12).

Figure 13:
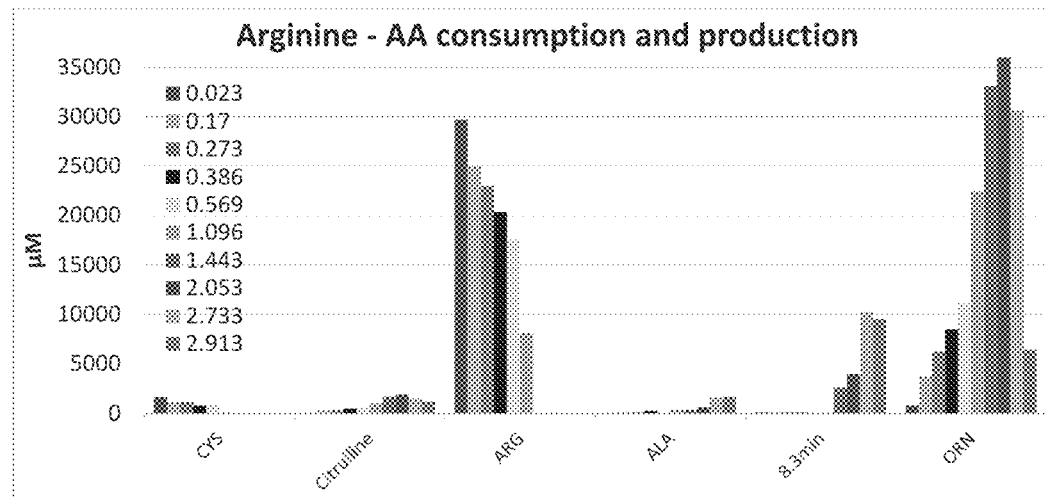
FIG. 13 is a graph showing amino acid consumption and production data for *C. autoethanogenum* DSM10061 in 5 g arginine/L+5 g fructose/L. Label denotes OD at sampling; μM unit not applicable to the 8.3 min peak.

FIG. 13 shows rapid utilization of arginine. In addition to accumulation of alanine, small amounts (~0.5 mM) of lysine and valine were produced similar to 4AA medium. The same unknown peak (8.3 min retention time) seen on the 4AA medium showed increasing peak areas after arginine depletion.

Figure 14:
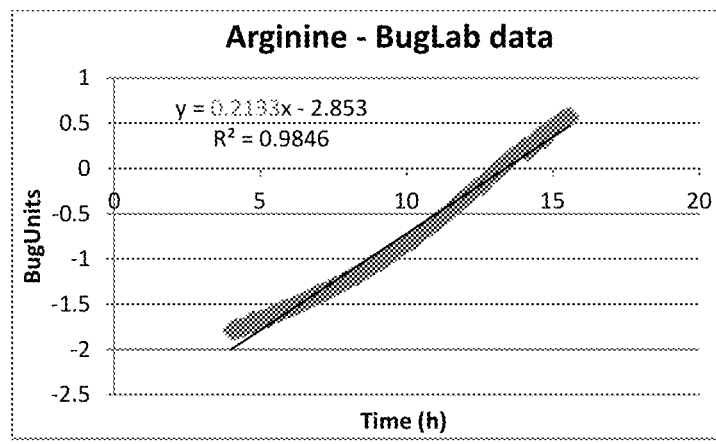
FIG. 14 is a graph showing growth data for *C. autoethanogenum* DSM10061 in YE-free PETC-MES media with 5 g arginine/L+5 g fructose/L using BugLab. BugUnits, ln of raw data. Specific growth rate 0.21 h-1 is tD~3 h.
Figure 15:
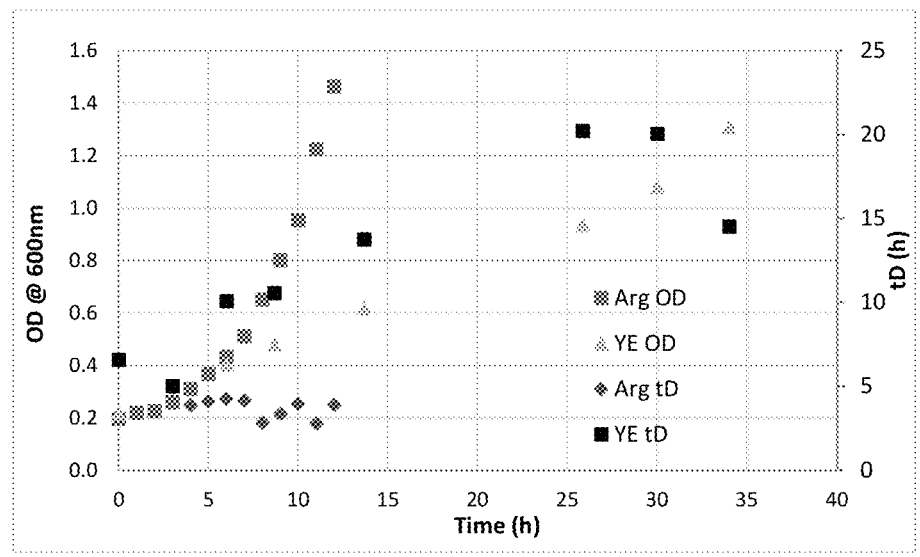
FIG. 15 is a graph showing the difference in growth curve and doubling times of arginine and yeast extract in bioreactor experiments with fructose.

To obtain a more accurate value of tD on Arginine medium, a BugLab experiment was performed to continuously monitor the increase of biomass before arginine runs out. This experiment confirmed the fast growth before arginine runs out as tD was calculated to be ~3 h (FIG. 14). Faster growth on Arginine compared to Yeast extract is demonstrated in FIG. 15.

Example 2

Enhanced Autotrophic Growth with Arginine Supplementation

This example demonstrates increased specific growth rate and less acetate production for acetogen $Clostridium$ $autoethanogenum$ DSM 23693 under autotrophic growth when supplemented with arginine.

$Clostridium$ $autoethanogenum$ DSM 23693 (a derivate of $Clostridium$ $autoethanogenum$ DSM 10061; US patent 2013/0217096) was sourced from DSMZ (The German Collection of Microorganisms and Cell Cultures, Inhoffenstraße 7 B, 38124 Braunschweig, Germany).

Growth was carried out in PETC-MES medium without yeast extract (Table 1) using standard anaerobic techniques (Hungate, $Meth$ $Microbiol$, 3B: 117-132, 1969; Wolfe, $Adv$ $Microb$ $Physiol$, 6: 107-146, 1971) and 22 psi of $CO/CO_2/H_2$ gas mix (composition: 50% CO, 20% $CO_2$, 2% $H_2$, 28% $N_2$) headspace pressure.

To study effect of supplementation with arginine, 5 g/L of arginine was added to the media and culture growth and metabolite production during autotrophic growth was compared to the control without arginine.

Growth was followed by measuring the optical density using a Thermo Genesys 20 spectrophotometer. Metabolites acetate (acetic acid), ethanol, 2,3-butanediol or lactic acid were measured by high-performance liquid chromatography (HPLC) on an Agilent LC with refractive index (RI) detection at 35° C. Samples were prepared by diluting 400 μL with 100 μL of 5-sulfosalicylic acid solution (1% w/v in 1 M sulphuric acid), followed by a 3 minute centrifugation at 14,000 rpm; the supernatant was transferred to a glass vial for analysis. Separation was carried out with a 10 μL injection on to an Alltech IOA-2000 column (150 mm×6.5 mm×8 μm) at 0.7 mL/min and 65° C. under isocratic conditions, using 5 mM sulphuric acid mobile phase.

The experiment was carried out in two biological repeats with triplicate cultures (n=3) for each condition in a volume of 40 mL media in 1 L Schott bottles at 37° C. with orbital shaking (120 rpm, shake orbit). In each case, acetogenic strain $C.$ $autoethanogenum$ DSM 23693 was pre-cultured in PETC-MES without yeast extract to an OD600 nm of 0.3 and a single preculture was used for inoculation.

In the first experiment to the following conditions: PETC-MES without yeast extract+22 psi syngas (initial OD600 nm=0.005) and PETC-MES without yeast extract+22 psi syngas+5 g arginine/L (initial OD600 nm=0.005).

In the repeat of the experiment, a culture was also inoculated into arginine supplemented media but without the addition of CO/CO2/H2 gas (22 psi of 100% N2 as headspace). This experiment comprised the following three conditions: PETC-MES without yeast extract+22 psi syngas (initial OD600 nm=0.03), PETC-MES without yeast extract+22 psi syngas+5 g arginine/L (initial OD600 nm=0.003), and PETC-MES without yeast extract+5 g arginine/L (initial OD600 nm=0.003). Media containing arginine were inoculated to a lower initial density than media without arginine to accommodate for the surprisingly increased specific growth rate with arginine observed in the first experiment.

Figure 16:
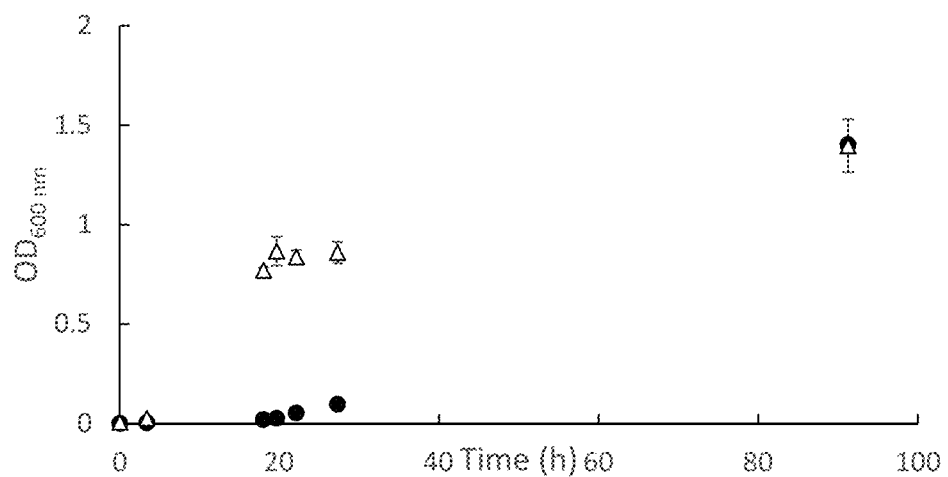
FIG. 16 is a graph showing autotrophic growth of *C. autoethanogenum* DSM 23693 with (Δ) and without (●) arginine supplementation.

In both experiments, cultures with arginine grew surprisingly rapidly (4 doublings in <15 h corresponding to a doubling time of tD=3.5 h and specific growth rate µ=0.198) until OD600 nm≈0.8, whereas growth of the control was much slower, with a doubling time tD=7.3 h and specific growth rate p=0.095 (FIG. 16+17). Arginine supplementation decreased the doubling time and increased specific growth rate of the culture during autotrophic growth therefore by over 50%.

Figure 18:
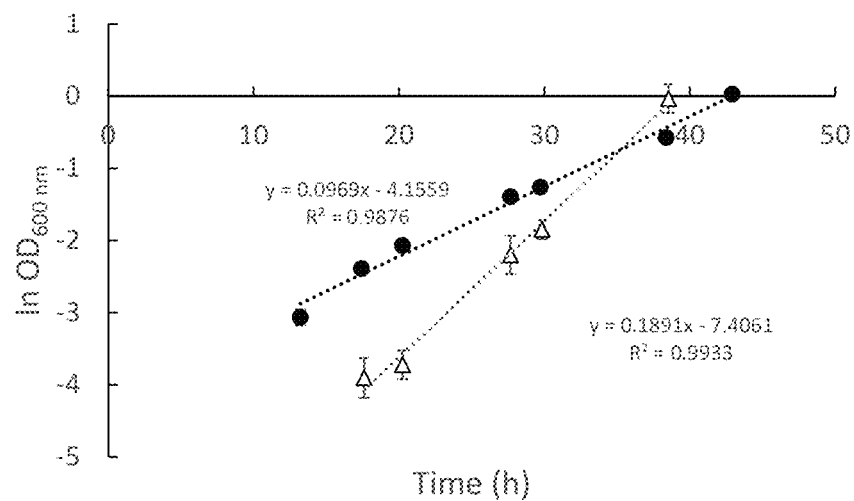
FIG. 18 is a Log plot of autotrophic growth of *C. autoethanogenum* DSM 23693 with (Δ) and without (●) arginine supplementation.

A log-transformed plot of autotrophic growth of *C. autoethanogenum* clearly demonstrates decreased doubling time from arginine supplementation (FIG. 18). Calculated doubling times are tD=7.3 h+0.2 for autotrophic growth without arginine supplementation and tD=3.5 h+0.2 with arginine supplementation, a decrease of 52%.

Figure 17:
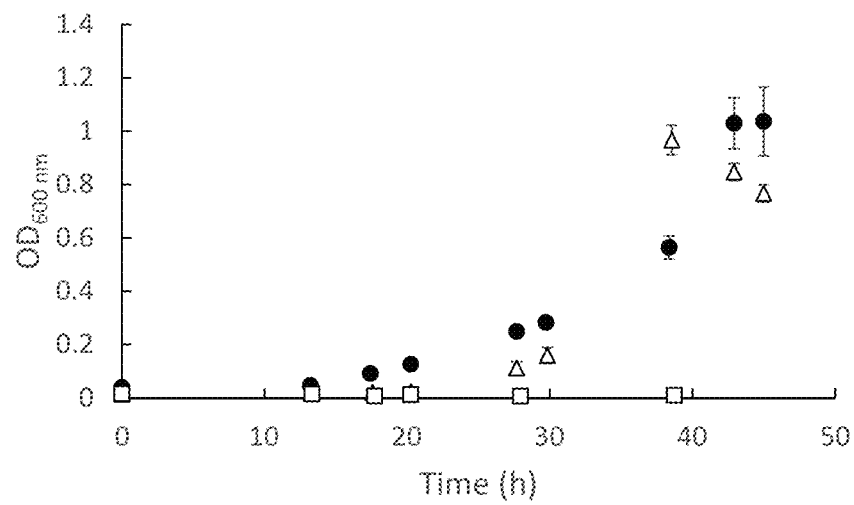
FIG. 17 is a graph showing autotrophic growth of *C. autoethanogenum* DSM 23693 with (Δ) and without (●) arginine supplementation, as well as growth on arginine only in the absence of $CO/CO_2/H_2$ gas (□).

Both with and without arginine, the cultures reached the same final density during autotrophic growth, indicating that arginine was not used as a carbon source but only served to increase the specific growth rate (FIG. 16+17). This was also confirmed in the culture where no gas was supplied, no growth was observed in 48 hours in cultures supplemented with arginine but without the CO/CO2/H2 gas mix (FIG. 17). This supports the hypothesis that arginine is not used as a carbon source under these conditions, but rather the CO/CO2 is used as the carbon source and ATP is supplied by arginine metabolism.

Figure 19:
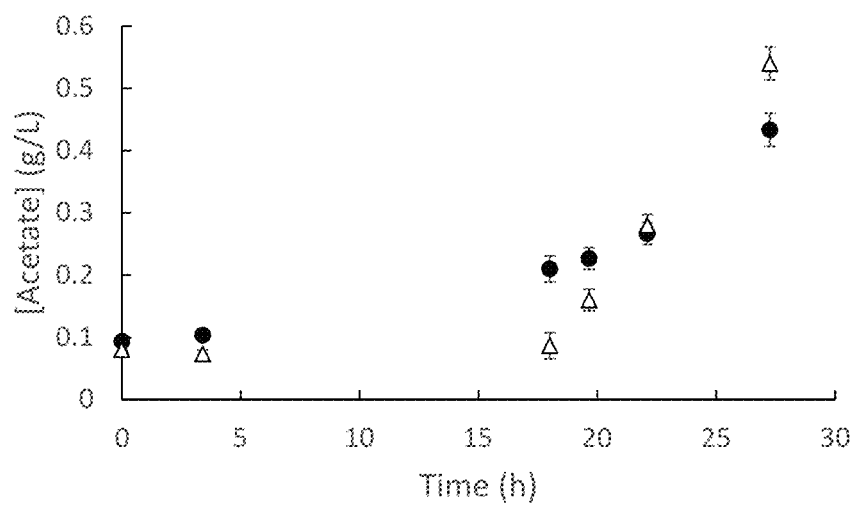
FIG. 19 is a graph showing acetate production during autotrophic growth of *C. autoethanogenum* DSM 23693 with (Δ) and without (●) arginine supplementation.
Figure 20:
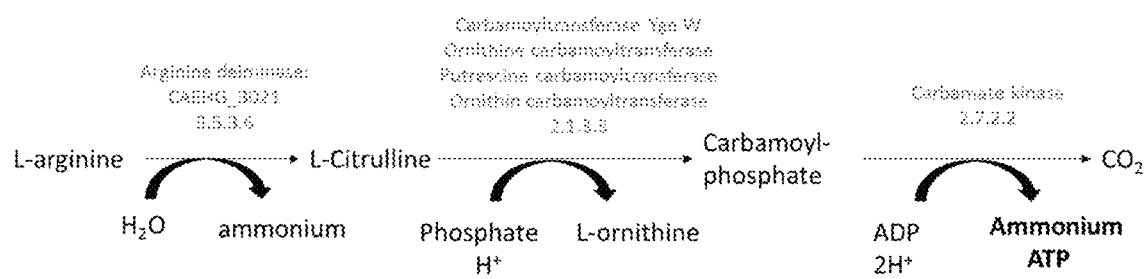
FIG. 20 is a schematic representation of the arginine decarboxylase pathway.

Autotrophic growth of acetogens is typically linked to acetate (acetic acid) production, as acetate formation generates ATP via substrate level phosphorylation in the acetate kinase reaction that is essential for growth. As such all isolated acetogens to date were found to produce acetate. However, acetate formation is not desirable from a process perspective as it diverts carbon away from target products and is known to be toxic to microorganisms already at low concentrations of a few percent (J. Ballongue, E. Masion, J. Amine, H. Petitdemange and R. Gay, *Appl. Microbiol. Biotechnol.*, 1987, 26, 568-573; G. Wang and D. I. Wang, *Appl. Environ. Microbiol.*, 1984, 47, 294-8). In growth medium supplemented with 5 g arginine/L, surprisingly no net acetate production was observed until the pause in growth at $OD_{600\ nm}$≈0.8 only at this stage acetate was produced (FIG. 19).

The results from this set of experiments suggest that *C. autoethanogenum* can utilize arginine to produce ATP for growth, and therefore does not need to produce acetate when arginine is supplied.

Example 3

Identification and Optimization of Arginine Utilization Pathways

This example demonstrates how arginine provide additional ATP for the cell and can be fed into the central metabolism of acetogens.

As demonstrated in example 1, Arginine is stoichiometrically converted to ornithine. Also citrulline accumulation was observed at some time points. Without wishing to be bound to this theory, this observation implicates arginine deiminase pathway as the mechanism.

This pathway would convert arginine into ornithine, ammonium, ATP, and CO2. Enhanced growth would be facilitated by the supply of ATP and ammonium from arginine degradation. This ATP supply also removes the need for acetogens to produce acetate.

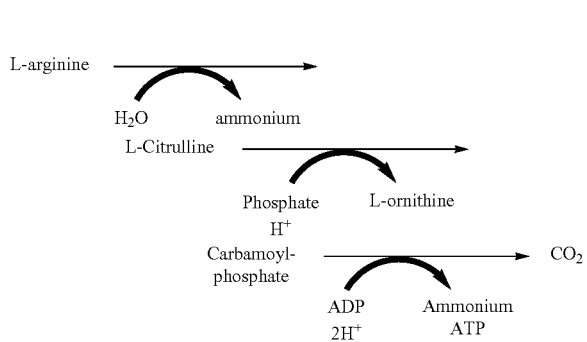

Arginine deiminase pathway proceeds via three enzymatic steps, catalysed by arginine deiminase (EC 3.5.3.6), ornithine carbomyltransferase (putrescine carbomyltransferase) (EC 2.1.3.3) and a carbamate kinase (EC 2.7.2.2). Respective enzymes (including two arginine/ornithine transporter genes/enzymes) have been identified in the genome of *C. autoethanogenum*, ornithine carbomyltransferase, and carbamate kinase is present in multiple copies (Table 4). Enzymes that are able to catalyse the same reactions are also present in other organisms including many acetogens including *C. ljungdahlii*, *C. scatologenes*, *C. drakei*, and *Acetonema longum* (Table 5). This pathway is also present in *C. stricklandii* or *E. coli*.

TABLE 4

Identified genes/enzymes of the arginine deiminase pathway in *C. autoethanogenum*

| Name | Nucleotide sequence (Genbank Gene ID accession number, Locus tag) | Amino acid sequence (Genbank Protein ID accession number) |
|---|---|---|
| arginine deiminase | 17336439, CAETHG_3021 | AGY77224 |
| ornithine carbomyltransferase | 17336440, CAETHG_3022 | AGY77225 |
|  | 17334022, CAETHG_0591 | AGY74820 |
| arginine/ornithine transporter | 17336441, CAETHG_3023 | AGY77226 |
|  | 17336442, CAETHG_3024 | AGY77227 |
| carbamate kinase | 17336443, CAETHG_3025 | AGY77228 |
|  | 17333852, CAETHG_0421 | AGY74650 |
|  | 17333876, CAETHG_0445 | AGY74674 |
|  | 17337050, CAETHG_3632 | AGY77835 |
|  | 17335507, CAETHG_2081 | AGY76300 |

TABLE 5

Identified genes/enzymes of the deiminase pathway in other organisms

| Organism | Accession number |
|---|---|
| Arginine deiminase | |
| Clostridium ljungdahlii DSM | ADK13995.1 |
| Clostridium scatologenes | AKA70116.1 |
| Clostridium drakei | WP_032076790.1 |
| Propionispira raffinosivorans | WP_026329241.1 |
| Acetonema longum | WP_040292494.1 |
| Clostridium perfringens | WP_003479447.1 |
| Clostridium sticklandii | WP_013361144.1 |
| Clostridium cadaveris | WP_051196258.1 |
| Clostridium colicanis | WP_002599585.1 |
| Caldisalinibacter kiritimatiensis | WP_006311966.1 |
| Caloranaerobacter azorensis | WP_035161638.1 |
| Halothermothrix orenii | WP_012635610.1 |
| Filifactor alocis | WP_014262361.1 |
| Dethiosulfovibrio peptidovorans | WP_005659654.1 |
| Aminomonas paucivorans | WP_006299755.1 |
| Clostridiisalibacter paucivorans | WP_026893703.1 |
| Thermanaerovibrio velox | WP_006582950.1 |
| Thermanaerovibrio acidaminovorans | WP_012870198.1 |
| Peptoniphilus indolicus | WP_004823213.1 |
| Borrelia hermsii | WP_038443653.1 |
| Borrelia hermsii YBT | AHH12878.1 |
| Borrelia hermsii | WP_043924507.1 |
| Borrelia hermsii HS1 | AAX17338.1 |
| Enterococcus phoeniculicola | WP_010766746.1 |
| Vagococcus lutrae | WP_023606773.1 |
| Borrelia hermsii | WP_025400143.1 |
| Borrelia parkeri | WP_025375819.1 |
| Brachyspira alvinipulli | WP_028331136.1 |
| Borrelia persica | WP_038363688.1 |
| Borrelia hispanica | WP_038359270.1 |
| Borrelia coriaceae | WP_025408405.1 |
| Borrelia turicatae | WP_011772777.1 |
| Fervidicella metallireducens | WP_035377985.1 |
| Carnobacterium divergens | WP_034570618.1 |
| Borrelia crocidurae | WP_038442698.1 |
| Borrelia duttonii | WP_038366702.1 |
| Borrelia duttonii | WP_012538581.1 |
| Borrelia crocidurae | WP_014696655.1 |
| Thermobrachium celere | WP_018660497.1 |
| Enterococcus faecalis | WP_048941938.1 |
| Enterococcus faecalis CBRD01 | ESU74366.1 |
| Borrelia recurrentis | WP_012539214.1 |
| Caloramator sp. ALD01 | WP_027308491.1 |
| Enterococcus faecalis | WP_002410400.1 |
| Caloramator australicus | WP_008907964.1 |
| Atopobacter phocae | WP_025729241.1 |
| Clostridium sulfidigenes | WP_035132876.1 |
| Borrelia anserina | WP_025419989.1 |
| Tetragenococcus halophilus | WP_014125833.1 |
| Enterococcus haemoperoxidus | WP_010761089.1 |
| Streptococcus marimammalium | WP_018369865.1 |
| Tetragenococcus muriaticus | WP_038024314.1 |
| Enterococcus gallinarum | WP_029486596.1 |
| Clostridium dakarense | WP_042277345.1 |
| Borrelia miyamotoi | WP_020955199.1 |
| Thermoanaerobacterium aotearoense | WP_014757694.1 |
| Streptococcus parauberis | WP_003104748.1 |
| Enterococcus casseliflavus | WP_010748983.1 |
| Clostridium botulinum | WP_011987187.1 |
| Streptococcus porcinus | WP_003083226.1 |
| Enterococcus casseliflavus | WP_005230691.1 |
| Borrelia miyamotoi | WP_025443390.1 |
| Thermoanaerobacterium xylanolyticum | WP_013786994.1 / WP_008087965.1 |
| Streptococcus ictaluri | WP_007892646.1 |
| Streptococcus pseudoporcinus | WP_017413713.1 |
| Clostridium tunisiense | |
| Ornithine carbomyltransferase | |
| Clostridium ljungdahlii | WP_013239445.1 |
| Propionispira raffinosivorans | WP_019552618.1 |
| Clostridium scatologenes | WP_046066002.1 |
| Acetonema longum | WP_004092025.1 |
| Clostridium senegalense | WP_010298035.1 |
| Clostridium argentinense | WP_039635916.1 |
| Clostridium argentinense | WP_039634993.1 |
| Candidatus Cloacimonas acidaminovorans | WP_015423864.1 |
| Clostridium senegalense | WP_010293963.1 |
| Clostridium botulinum | WP_041345924.1 |
| Staphylococcus haemolyticus | WP_053016198.1 |
| Clostridium tunisiense | WP_017413712.1 |
| Staphylococcus simulans | WP_023016208.1 |
| Clostridium sporogenes | WP_058009868.1 |
| Staphylococcus haemolyticus | WP_053030082.1 |
| Staphylococcus carnosus | WP_012664052.1 |
| Staphylococcus epidermidis | WP_049386361.1 |
| Staphylococcus carnosus | WP_053464819.1 |
| Clostridium drakei | WP_032079337.1 |
| Staphylococcus capitis | WP_002452600.1 |
| Bacillus rubiinfantis | WP_042357582.1 |
| Staphylococcus carnosus | WP_046100679.1 |
| Staphylococcus aureus | WP_031891031.1 |
| Lactobacillus rennini | WP_057873389.1 |
| Staphylococcus microti | WP_044360832.1 |
| Streptococcus agalactiae | WP_000793624.1 |
| Lactobacillus parabrevis | WP_020089358.1 |
| Carbamate kinase | |
| Clostridium scatologenes | WP_029954845.1 |
| Clostridium drakei | WP_032079746.1 |
| Clostridium argentinense | WP_039633500.1 |
| Clostridium carboxidivorans | WP_007061333.1 |
| Clostridium drakei | WP_032075357.1 |
| Clostridium scatologenes | WP_029162276.1 |
| Thermoanaerobacter thermocopriae | WP_028991790.1 |
| Thermoanaerobacter mathranii | WP_013149923.1 |
| Thermoanaerobacter italicus | WP_012994659.1 |
| Caldanaerobacter subterraneus | WP_022588163.1 |
| Caldanaerobacter subterraneus | WP_011024959.1 |
| Acetonema longum | WP_004092029.1 |
| Thermoanaerobacter siderophilus | WP_006569095.1 |
| hypothetical protein [Propionispira raffinosivorans] | WP_019552620.1 |
| Thermoanaerobacter thermocopriae | WP_054644772.1 |
| Thermoanaerobacter wiegelii | WP_014062398.1 |
| Thermoanaerobacter kivui | WP_049684636.1 |
| Thermoanaerobacterium thermosaccharolyticum | WP_013298601.1 |
| Caldisalinibacter kiritimatiensis | WP_006311968.1 |
| Thermoanaerobacterium thermosaccharolyticum | WP_015312281.1 |
| Eubacterium nodatum | WP_034819233.1 |
| Thermanaerovibrio velox | WP_006584132.1 |
| Thermanaerovibrio acidaminovorans | WP_012869022.1 |
| Aminiphilus circumscriptus | WP_026369063.1 |
| Clostridium argentinense | WP_039635912.1 |
| Anaerovorax odorimutans | WP_027398659.1 |
| Thermoanaerobacterium xylanolyticum | WP_013787463.1 |
| Clostridium aerotolerans | WP_026892136.1 |
| Fervidicella metallireducens | WP_035377990.1 |
| Clostridium argentinense | WP_039636739.1 |
| Clostridium senegalense | WP_010298030.1 |
| Clostridium sphenoides | WP_054791734.1 |
| Clostridiales bacterium oral taxon 876 | WP_021654611.1 |
| Clostridium perfringens | WP_025648248.1 |
| Clostridium sp. KNHs214 | WP_035294990.1 |
| Clostridium perfringens | WP_003457589.1 |
| Thermoanaerobacterium aotearoense | WP_014759446.1 |
| Clostridium celerecrescens | WP_038281265.1 |
| Alkaliphilus metallliredigens | WP_049765320.1 |
| Clostridium botulinum | WP_024932088.1 |
| Clostridium algidicarnis | WP_029453364.1 |
| Clostridium botulinum | WP_012669533.1 |
| Clostridium drakei | WP_032077363.1 |
| Clostridium sticklandii | WP_013361146.1 |

To increase performance, in particular if accumulation of intermediates as citruline is observed, of the pathway, respective genes can be overexpressed or genes from other sources can be introduced and heterologously expressed by someone skilled in the art using methods described before [US 2013/344547, US 2013/330809, US 2013/323820, US 2013/224838, US 2013/224839, US 2011/256600, US 2011/236941.

Ornithine itself can be further converted to alanine, which has been shown to accumulate as well in example 1. This conversion also generates additional reducing equivalents NADP(H), as well as another molecule of ammonia and key building block acetyl-CoA from CoA.

As shown in Figure. 23, ornithine conversion to alanine and acetyl-CoA proceeds via enzymatic steps ornithine racemase (EC 5.1.1.12), ornithine aminomutase (EC 5.4.3.5), 2,4-diaminopentanoate dehydrogenase (EC 1.4.1.12) and 2-amino-4-oxopentanoate thiolase (EC 2.3.1.B10). Respective enzymes have been described for example from *Clostridium sticklandii* or environmental samples and homologues have been identified in *C. autoethanogenum* (Table 6).

TABLE 6

Identified genes/enzymes of the ornithine to alanine and acetyl-CoA conversion pathway from *C. sticklandii* or environmental samples and *C. autoethanogenum* homologues.

| Name | Nucleotide sequence (Genbank Gene ID accession number, locus tag) | Amino acid sequence (Genbank Protein ID accession number) |
| --- | --- | --- |
| ornithine racemase | 9854830, CLOST_1288 | CBH21408 |
| ornithine aminomutase, subunit beta (OraE) | 9854831, CLOST_1290 17333626, CAETHG_0193 | CBH21410 AGY74426 |
| ornithine aminomutase, subunit alpha (OraS) | 9856217, CLOST_1291 | CBH21411 |
| 2,4-diaminopentanoate dehydrogenase | CU695246 | CAQ42978.1 |
| 2-amino-4-oxopentanoate thiolase, beta subunit | CU695248 | CAQ42980.1 |
| 2-amino-4-oxopentanoate thiolase, alpha subunit | CU695247 | CAQ42979.1 |

To increase performance of the pathway, in particular as accumulation of ornithine was observed, respective *C. autoethanogenum* genes can be overexpressed or genes from *C. sticklandii* or environmental samples of table 6 can be introduced and heterologously expressed by someone skilled in the art using methods described before (W2012/053905, WO2012/115527, WO2013/180584). The organism may also be adapted and evolved to utilize ornithine more effectively if it is adapted for growth on arginine over time.

To achieve flux into the pathway it may also be necessary to knock-out the arginine:ornithine transporter (CAETHG_3023-24) to avoid ornithine getting exported out of the cell. Such knockouts can be achieved by someone skilled in the art using methods described before (W2012/053905, WO2012/115527, and WO2013/180584). It may further become needed to add an alternative arginine transporter. An alternative approach to knock-out the arginine:ornithine transporter could be to introduce an ornithine importer, so ornithine can be metabolized further.

The identified pathways were also simulated in a genome scale model reconstruction to show the effect of the metabolism and confirm the identified pathways.

A genome-scale metabolic reconstruction for *C. autoethanogenum* was generated based on published methods (L.-E. Quek and L. K. Nielsen, Genome Inform., 2008, 21, 89-100; C. G. de Oliveira Dal'Molin, L.-E. Quek, R. W. Palfreyman, S. M. Brumbley and L. K. Nielsen, Plant Physiol., 2010, 152, 579-89; C. Licona-Cassani, E. Marcellin, L.-E. Quek, S. Jacob and L. K. Nielsen, Antonie Van Leeuwenhoek, 2012, 102, 493-502.). The core of the genome-scale model was reconstructed using the SEED model annotation pipeline (C. S. Henry, M. DeJongh, A. A. Best, P. M. Frybarger, B. Linsay and R. L. Stevens, Nat. Biotechnol., 2010, 28, 977-82). The reconstruction retained all reaction attributes from SEED model, including unique reactions, compound IDs and the reversibility of reactions. The model was manually gap filled in Excel (Microsoft Corporation) for ease of annotation and commenting, in particular, central metabolism and above identified arginine utilization pathways were manually curated. From this gene-centric database, a 2D reaction-centric SBML (System Biology Markup Language, http://www.sbml.org) representation was generated using a Java (Oracle Corporation) application. Constraint-based reconstruction and analysis was performed using the COBRA toolbox (http://opencobra.sourceforge.net/) (J. Schellenberger, R. Que, R. M. T. Fleming, I. Thiele, J. D. Orth, A. M. Feist, D. C. Zielinski, A. Bordbar, N. E. Lewis, S. Rahmanian, J. Kang, D. R. Hyduke and B. Ø. Palsson, Nat. Protoc., 2011, 6, 1290-307). A set of scripts for constraint-based modelling run within the MATLAB environment. Flux balance analysis (Orth et al., 2010) was used to predict essential nutrients for growth, and a shadow price analysis was performed to investigate the beneficial effects of Amino Acids (AA) on *Clostridium autoethanogenum*, and to determine which AA have the greatest impact on ATP production. Flux balance analysis (FBA) has been used for predicting essential nutrients for growth (Fan et al., 2014; Song et al., 2008), effects of AA supplementation on target product synthesis (Licona-Cassani et al., 2012) and in conjunction with shadow price analysis (Hillier and Lieberman, 2010) to determine substrates having the biggest effect on ATP production (Teusink et al., 2006).

Conventional shadow price analysis can be misleading with AAs. If shadow price analysis is performed around autotrophic conditions (i.e. at zero uptake), it will show the opportunity cost of AA synthesis, i.e., the resources that could be released if a given AA was supplied by the medium. The most expensive AA to synthesise is not necessarily the best substrate for ATP production. For example, there may be no degradation pathway available.

In order to overcome this issue, an offset shadow price analysis was performed. Each of the 20 AAs were allowed a maximum flux of 1.4 mmol/gDCW/h while maximising for biomass yield. This flux is the observed maximal specific fructose uptake rate of *C. autoethanogenum* DSM 10061 during preliminary growth experiments on standard PETC-MES medium (including yeast extract (YE)) and fructose. AAs with no degradation pathway cannot utilise the maximum allowed flux and hence will have zero shadow price. Shadow price analysis identified nine AAs—glutamine, histidine (HIS), cysteine (CYS), threonine, aspartate (ASP), arginine (ARG), glycine, serine and glutamate (GLU)—from the conventional 20 which *C. autoethanogenum* should prefer as they lead to faster growth.

The model prediction of AA was confirmed on a 20AA medium for eight of the predicted nine AAs (FIG. 2), excluding only glycine. Notably, uptake of ASP, GLU, HIS and ARG per biomass was more than 20-fold higher than needed for biomass synthesis. AA uptake per gram biomass was compared to the expected concentration in biomass (the cellular requirement), based on measurements taken in *Clostridium acetobutylcium* (Lee et al., 2008).

Surprisingly, on a further designed 12AA medium, it was found that the uptake of ASP, GLU, HIS and ARG was more than 120-fold higher than needed for biomass synthesis and that they enable significantly faster growth. This indicates the potential involvement of ASP, GLU, HIS and ARG in energy generation. Interestingly, concomitantly with arginine consumption during the fast growth phase, accumulation of ornithine was detected (FIG. 8) pointing towards the potential involvement of the arginine deiminase (ADI) pathway in providing cells with extra ATP. It is noteworthy that the initially observed fast growth (tD=2.5±0.1 h) is very close to the predicted growth with 20 AAs (tD=2.9 h).

Interestingly, substantially lower acetate production per biomass was observed in media containing ASP, GLU, HIS and ARG (4AA medium) (8.2±0.2 mmol/gDCW) and medium containing Arginine only (ARG medium) (6.7±0.7 mmol/gDCW) during growth when Arginine was abundant compared to YE (36.6 mmol/gDCW). Acetate production strongly increased after Arginine depletion (46.5±11.2 and 34.5±9.3 mmol/gDCW for 4AA medium and ARG medium, respectively) demonstrating that the possibility to catabolise arginine strongly reduces the necessity for an acetogen to produce acetate.

Figure 21:
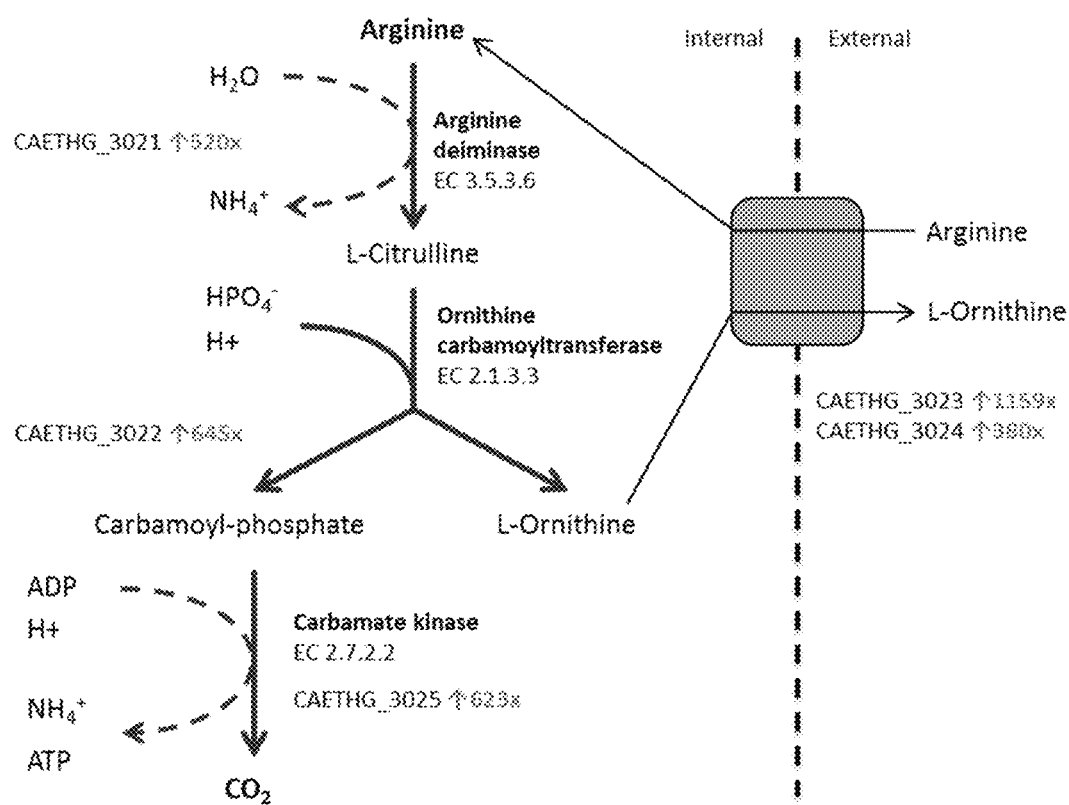
FIG. 21 is a schematic representation of L-arginine degradation in an arginine deiminase pathway.
Figure 22A:
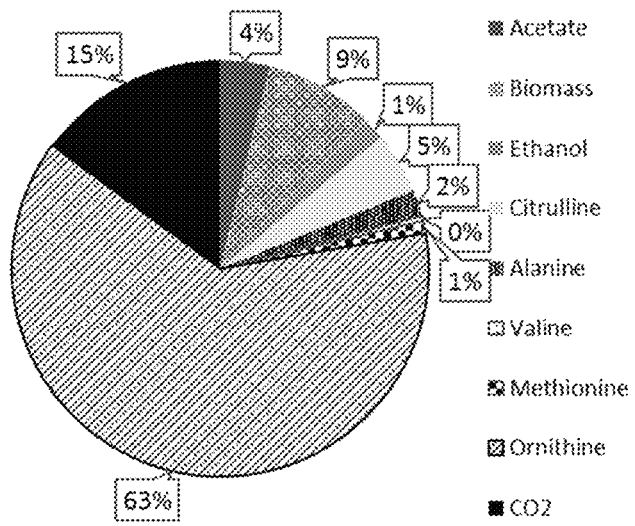
FIG. 22A and FIG. 22B are pie charts showing the carbon flux to products.
Figure 22B:
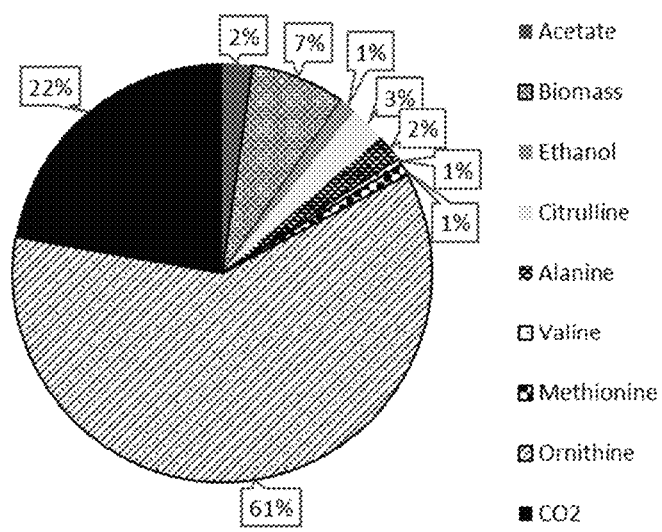

Heterotrophic cultures of C. autoethanogenum grown on 12AA medium accumulated ornithine concomitantly with arginine consumption (FIG. 8). The same was seen in 4AA medium and arginine only medium bioreactor experiments with a high fraction of (approximately 60%) of the consumed carbon excreted as ornithine (FIG. 22). In addition, significant carbon flux to $CO_2$ and also a notable accumulation of citrulline was detected. Other minor by-products included acetate, alanine, and ethanol. Altogether, significant carbon fluxes to ornithine, $CO_2$, and citrulline suggest that arginine was catabolised through the ADI pathway, explaining its growth-boosting effect through the supply of ATP (FIG. 21). Furthermore, the complete stoichiometric conversion of arginine into ornithine, $CO_2$, and citrulline implies that arginine was metabolised strictly to generate energy and not to synthesise biomass. This is consistent with the result of no growth observed when only arginine was supplemented to the YE-free PETC-MES containing Schott bottles pressurised with $N_2$ gas.

The involvement of the ADI pathway in facilitating faster growth was predicted by the initial in silico simulations on 4AA and arginine only medium. The total specific ATP production rate ($q_{ATP}$; mmol ATP/gDCW/h) was predicted to be approximately 6-fold higher in the latter conditions (SIM 4 and 5) compared to calculations with fructose (SIM 1) as the only carbon source (Table 7). The same was observed when the model was constrained with experimentally determined substrate uptake and product secretion rates (excluding citrulline and $CO_2$) from the bioreactor experiments on 4AA (SIM6 and 9) and arginine (SIM 12 and 15) only media, with approximately 3-4-fold higher $q_{ATP}$ than predicted solely on fructose. The observed faster growth ($t_D$~3-4 h) on AAs compared to the predicted growth without AA supplementation ($t_D$~14 h) can be explained by significantly higher energy production from substrate-level phosphorylation during arginine catabolism (by carbamate kinase of the ADI pathway) and indirectly through the generation of a proton-motive force by the production and excretion of $NH_4^+$. The latter is also beneficial for decreasing bioprocess costs by the reduced need to neutralise pH with $NH_4OH$ addition.

TABLE 7

Model simulations to predict specific growth rate, ATP production rates and products during heterotrophic growth with and without arginine supplementation:

| | SIM 1 | SIM 4 | SIM 5 | SIM 6 | SIM 7 | SIM 9 | SIM 10 | SIM 12 | SIM 13 | SIM 15 | SIM 16 |
|---|---|---|---|---|---|---|---|---|---|---|---|
| Specific substrate uptake rate (mmol/gDCW/h) | | | | | | | | | | | |
| Fructose | 1.40 | 1.40 | 1.40 | 1.99 | 1.99 | 1.48 | 1.48 | 1.43 | 1.43 | 1.40 | 1.40 |
| Aspartate | 0.00 | 1.40 | 0.00 | 0.76 | 0.76 | 0.85 | 0.85 | 0.00 | 0.00 | 0.00 | 0.00 |
| Histidine | 0.00 | 1.40 | 0.00 | 0.13 | 0.13 | 0.41 | 0.41 | 0.00 | 0.00 | 0.00 | 0.00 |
| Glutamate | 0.00 | 1.40 | 0.00 | 0.63 | 0.63 | 0.63 | 0.63 | 0.39 | 0.39 | 0.00 | 0.00 |
| Cysteine | 0.00 | 1.40 | 1.40 | 3.95 | 3.95 | 2.09 | 2.09 | 1.30 | 1.30 | 1.06 | 1.06 |
| Arginine | 0.00 | 10.00 | 10.00 | 19.11 | 19.11 | 13.10 | 13.10 | 10.22 | 10.22 | 11.99 | 11.99 |
| Specific product excretion rate (mmol/gDCW/h) | | | | | | | | | | | |
| Acetate | 3.15 | 35.97 | 28.15 | 2.03 | 55.01 | 1.97 | 37.78 | 1.38 | 28.47 | 1.14 | 31.77 |
| Ethanol | 0.00 | 0.00 | 0.00 | 0.89 | 0.00 | 0.82 | 0.00 | 0.97 | 0.00 | 0.65 | 0.00 |
| Carbon dioxide | 0.11 | 9.06 | 5.38 | 22.51 | 13.75 | 15.58 | 9.82 | 11.45 | 6.56 | 12.48 | 7.16 |
| Ornithine | 0.00 | 0.00 | 0.00 | 19.10 | 0.00 | 12.71 | 0.00 | 9.49 | 0.00 | 11.02 | 0.00 |
| Alanine | 0.00 | 0.00 | 0.00 | 0.89 | 0.00 | 0.71 | 0.00 | 0.66 | 0.00 | 0.69 | 0.00 |
| Lactate | 0.00 | 0.00 | 0.00 | 0.00 | 0.00 | 0.00 | 0.00 | 0.00 | 0.00 | 0.00 | 0.00 |
| Citrulline | 0.00 | 0.00 | 0.00 | 1.05 | 0.00 | 0.81 | 0.00 | 0.45 | 0.00 | 0.46 | 0.00 |
| 2,3-butanediol | 0.00 | 0.00 | 0.00 | 0.00 | 0.00 | 0.00 | 0.00 | 0.00 | 0.00 | 0.00 | 0.00 |
| 2-oxobutarate | 0.00 | 0.00 | 0.00 | 0.48 | 0.00 | 0.27 | 0.00 | 0.03 | 0.00 | 0.00 | 0.00 |
| Formamide | 0.00 | 1.38 | 0.00 | 0.11 | 0.09 | 0.39 | 0.38 | 0.00 | 0.00 | 0.00 | 0.00 |
| Specific growth rate ($h^{-1}$) | 0.05 | 0.28 | 0.17 | 0.25 | 0.54 | 0.24 | 0.43 | 0.19 | 0.31 | 0.19 | 0.32 |
| Total specific ATP production rate (mmol/gDCW/h) | 6.80 | 45.57 | 38.55 | 34.81 | 72.08 | 23.82 | 49.11 | 18.92 | 37.70 | 20.83 | 42.40 |

The fast growth and low acetate synthesis realised through arginine supplementation is relevant for the biotechnology industry as diminishing carbon flux to the unwanted by-product acetate and production of extra ATP from alternative pathways is essential for expanding the product spectrum of acetogens.

Genome Scale Models can be used to estimate intracellular metabolic flux patterns and calculate carbon, redox and energy balances by constraining the model with experimentally measured data (Bordbar et al., 2014; Dash et al., 2016; O'Brien et al., 2015). A genome-scale metabolic model of *C. autoethanogenum* similar to the one described by Marcellin (Low carbon fuels and commodity chemicals from waste gases—Systematic approach to understand energy metabolism in a model acetogen, Green Chem, 2016) was utilized. Genome scale model analysis we performed for the heterotrophic experiments on AA medium and arginine only medium by performing Flux balance analysis calculations as described above. The model was additionally constrained with specific substrate uptake and product secretion rates (excluding citrulline and CO2), and the cellular tD. Maximisation of ATP dissipation (i.e. unaccounted ATP costs; see below) was used as the objective function to perform FBA (no maintenance energy costs were included here).

Figure 24:
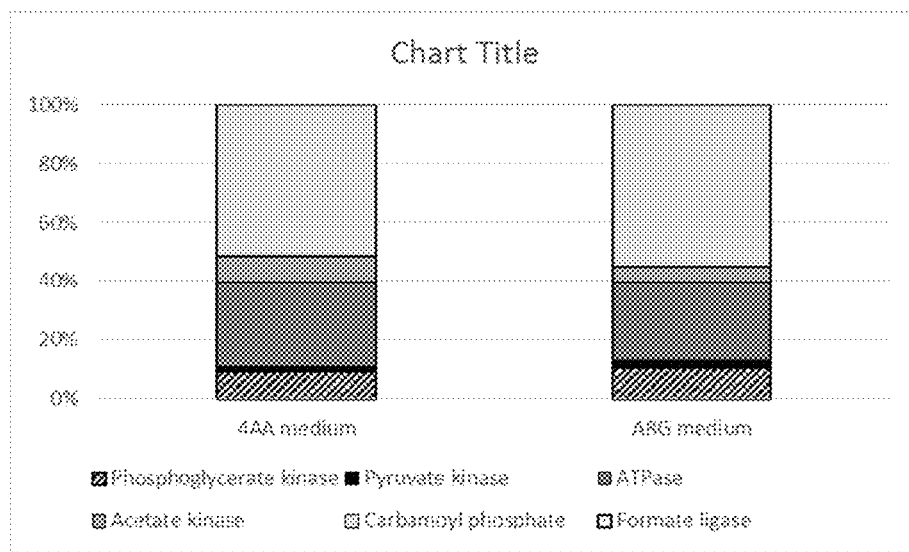
FIG. 24 is a chart showing distribution of ATP production during heterotrophic growth of *C. autoethanogenum* on 4AA or ARG media with fructose.

Fast growth on 4AA medium and ARG medium was facilitated by the approximately 3- to 4-fold higher $q_{ATP}$ (29.3±5.5 and 19.9±1.0 mmol ATP/gDCW/h for 4AA medium and ARG medium, respectively; (SIM6 and 9, and SIM12 and 15 in Table 7) compared to the value of 6.8 mmol ATP/gDCW/h predicted for growth solely on fructose (SIM1). The inventors consider that the faster growth observed on 4AA medium compared to ARG medium is explained by the 2-fold higher specific flux through the ATP-producing acetate kinase reaction (FIG. 24). However, on both media ~53% of ATP was produced via the ADI pathway (FIG. 24) which shows that arginine catabolism completely reorganised energy metabolism. Interestingly, although arginine consumption is favoured in many bacteria (Abdelal, 1979; Adamberg et al., 2006; Lahtvee et al., 2011; Mehmeti et al., 2011), its contribution to energy production is variable.

The predicted optimal flux pattern during heterotrophic growth on fructose and AAs was also analysed. When constraining the model with the experimentally measured substrate uptake rates and unaccounted ATP costs calculated previously, and maximising for biomass yield, these calculations predicted faster growth (4AA medium $t_D$=1.4±0.2 h, SIM 7 and 10; ARG medium $t_D$=2.2±0.1 h, SIM 13 and 16) compared to what was experimentally observed ($t_D$=2.8±0.1 h and $t_D$=3.7±0.0 h, respectively). Furthermore, in the simulations ornithine produced during arginine catabolism was catabolised to GLU, demonstrating that it is possible to further metabolizing ornithine via the above described pathway ornithine. The predicted faster growth thus comes from GLU catabolism to pyruvate using the methylaspartate pathway (as noted above) and its further conversion to acetyl-CoA and acetate yielding reduced Fd and ATP.

Example 4

Growth on Arginine as Sole Nitrogen Source

This example demonstrates the replacement of ammonium as nitrogen source with arginine.

Nitrogen is an essential nutrient for bacteria, and typically ammonium is used in fermentations and is also used as nitrogen source in published media formulations for acetogens (M. Köpke, C. Held, S. Hujer, H. Liesegang, A. Wiezer, A. Wollherr, A. Ehrenreich, W. Liebl, G. Gottschalk and P. Dürre, *Proc. Natl. Acad. Sci. U.S.A*, 2010, 107, 13087-92; J. Mock, Y. Zheng, A. P. Mueller, S. Ly, L. Tran, S. Segovia, S. Nagaraju, M. Köpke, P. Dürre and R. K. Thauer, *J. Bacteriol.*, 2015, 197, 2965-2980; H. Richter, M. E. Martin and L. T. Angenent, *Energies*, 2013, 6, 3987-4000; J. L. Cotter, M. S. Chinn and A. M. Grunden, *Bioprocess Biosyst. Eng.*, 2009, 32, 369-80.M. Straub, M. Demler, D. Weuster-Botz and P. Dürre, *J. Biotechnol.*, 2014.). However, ammonium production depends on plentiful supplies of energy, predominantly natural gas or liquefied petroleum gases (LPG) via the Haber-Bosch process (www.essentialchemicalindustry.org/chemicals/ammoinia.html) and thus not a sustainable source. In addition ammonium ions have an influence on the pH in the fermentation.

The identified pathway of example 3 allows conversion of 1 mol of arginine to 3 mol of ammonia. Thus arginine can provide an alternative nitrogen source for the bacteria, providing ammonia directly in the metabolism, while still providing advantages described above. Since 1 molecule of arginine can be broken down to 3 molecules of ammonia, lower quantities required lead to significant cost savings from cheaper price of arginine (99% food grade arginine costs around ~US$17-18,000/1000 kg while 30% industrial grade ammonia is ~US$10-11,000/1000 kg from Sigma Aldrich or Fisher) and reduced handling. In addition, arginine can be derived sustainable from biological sources, for example by fermentation (T. Utagawa, *J. Nutr.*, 2004, 134, 2854S-2857).

To demonstrate that arginine can be used as sole nitrogen source for acetogen *Clostridium autoethanogenum* DSM 23693 the organism is grown on YE-free PETC-MES medium omitting the 1 g/L ammonium chloride ($NH_4Cl$) with 0.33 g/L non-synthetic L-arginine monohydrochloride (Sigma Aldrich; A6969).

Example 5

Supplementation of Arginine Leads to Increased Production of Non-Natural Products from Heterologous Pathways, in Particular ATP Consuming Pathways This example demonstrates that supplementation of arginine increases production of non-natural products from heterologous pathways.

Production of several non-natural products have been demonstrated in acetogens from gas [W2012053905, WO2012115527, WO2013180584, WO2013185123, WO2013191567]. Typically some level of acetate is observed as byproduct, as the organism generates ATP from substrate level phosphorylation via the acetate kinase reaction. This is, in particular, the case for pathways that require ATP as for example but not limited to production pathways for isoprene or other terpenoides (mevalonate pathway), or production of fatty acid derived products like biodiesel (via fatty acid biosynthesis). However, it is also the case for other fermentation pathways that do not directly require ATP but also do not yield the same amount of ATP per acetyl-CoA as formation of acetate, for example, but not limited to production of isopropanol, acetone, butanol (via ABE pathway).

Production of isopropanol from gas was simulated using flux balance analysis (FBA) with the *C. autoethanogenum* genome scale model (described in example 3). Heterologous pathways (table 4) were added to the model and simulations on the maximum theoretical yield were carried out with and without arginine supplementation (table 5).

TABLE 8

Heterologous pathways

| name | equation |
|---|---|
| Mevalonate pathway and isoprene synthase | |
| thiolase | 2 Acetyl = CoA <=> CoA + Acetoacetyl = CoA |
| 3-HMG-CoA synthase | (S) = 3 = Hydroxy = 3 = methylglutaryl = CoA + CoA <=> Acetyl = CoA + Acetoacetyl = CoA |
| 3-HMG-CoA reductase (NADH) | (R) = Mevalonate + CoA + 2 NAD+ <=> (S) = 3 = Hydroxy = 3 = methylglutaryl = CoA + 2 NADH |
| 3-HMG-CoA reductase reductase (NADPH) | (R) = Mevalonate + CoA + 2 NADP+ <=> (S) = 3 = Hydroxy = 3 = methylglutaryl = CoA + 2 NADPH |
| Mevalonate kinase (ATP) | ATP + (R) = Mevalonate => ADP + (R) = 5 = Phosphomevalonate |
| Mevalonate kinase (CTP) | CTP + (R) = Mevalonate => CDP + (R) = 5 = Phosphomevalonate |
| Mevalonate kinase (GTP) | GTP + (R) = Mevalonate => GDP + (R) = 5 = Phosphomevalonate |
| Mevalonate kinase (UTP) | UTP + (R) = Mevalonate => UDP + (R) = 5 = Phosphomevalonate |
| Phosphomevalonate kinase | ATP + (R) = 5 = Phosphomevalonate => ADP + (R) = 5 = Diphosphomevalonate |
| Diphosphomevalonate decarboxylase | ATP + (R) = 5 = Diphosphomevalonate => ADP + Orthophosphate + Isopentenyl_diphosphate + CO2 |
| Isopentenyl-diphosphate Delta-isomerase | Isopentenyl_diphosphate <=> Dimethylallyl_diphosphate |
| Isoprene synthase | Dimethylallyl_diphosphate => Isoprene + PP |
| Isoprene transport | Isoprene (cyt) => Isoprene (ext) |
| isopropanol pathway | |
| thiolase | 2 Acetyl = CoA <=> CoA + Acetoacetyl = CoA |
| CoA transferase | Acetoacetyl = CoA + Acetate <=> Acetoacetate + Acetyl-CoA |
| acetoacetate decarboxylase | Acetoacetate => Acetone + CO2 |
| secondary alcohol dehydrogenase | Acetone + NADPH => Isopropanol |
| isopropanol transport | Isopropanol (cyt) => Isopropanol (ext) |

Table 9: FBA analysis of maximum theoretical yields of target products isoprene or isopropanol from CO and CO2/H2 with and without arginine supplementation in mmol/gDW/h:

| Target | CO — 60 mmol CO/gDW/h | | |
|---|---|---|---|
| Product | Product | Acetate | Ethanol |
| Isopropanol | 5.061008 | 0 | 2.408488 |
| Isoprene | 1.967815 | 2.209201 | 3.935631 |

| Target | CO + arginine — 60 mmmol CO + 2 mmol arginine/gDW/h | | |
|---|---|---|---|
| Product | Product | Acetate | Ethanol |
| Isopropanol | 6.41679498 | 0 | 2.041474197 |
| Isoprene | 2.576176316 | 2.254853944 | 4.152352632 |

| Target | CO + arginine — 48 mmol CO + 2 mmol arginine/gDW/h | | |
|---|---|---|---|
| Product | Product | Acetate | Ethanol |
| Isopropanol | 5.404593388 | 0 | 1.559776585 |
| Isoprene | 2.182613259 | 1.813013818 | 3.365226517 |

| Target | CO2/H2 — 60 mmol CO2/H2/gDW/h | | |
|---|---|---|---|
| Product | Product | Acetate | Ethanol |
| Isopropanol | 5.00758257 | 0 | 2.408488 |
| Isoprene | 1.26220128 | 2.209201 | 3.935631 |

| Target | CO2/H2 + arginine — 60 mmmol CO2/H2 + 2 mmol arginine/gDW/h | | |
|---|---|---|---|
| Product | Product | Acetate | Ethanol |
| Isopropanol | 6.361290323 | 0 | 2.041474 |
| Isoprene | 1.83911141 | 2.254854 | 4.152353 |

| Target | CO2/H2 + arginine — 48 mmol CO2/H2 + 2 mmol arginine/gDW/h | | |
|---|---|---|---|
| Product | Product | Acetate | Ethanol |
| Isopropanol | 5.359773808 | 0 | 1.559777 |
| Isoprene | 1.586671154 | 1.813014 | 3.365227 |

The simulation shows that arginine supplementation can significantly increase maximum theoretical production yields of targets compounds isopropanol and isoprene both on CO and CO2/H2. Maximum isopropanol production from CO could be significantly increased by more than 20% from 5.06 mmol/gDW/h to 6.42 mmol/gDW/h already with small amounts of arginine uptake (2 mM, 0.34 g/L). For ATP consuming mevalonate pathway for isoprene production from CO, maximum production could be increased even more significantly by over 30% from 1.97 mmol/gDW/h to 2.58 mmol/gDW/h. The effect is even more pronounced from CO2/H2, where maximum isopropanol production can be increased by over 25% from 5.0 mmol/gDW/h to 6.36 mmol/gDW/h and isoprene production by 45% from 1.26 mmol/gDW/h to 1.83 mmol/gDW/h. This clearly demonstrate that arginine can be used to boost production of non-natural target molecules.

The simulation also shows that when 2 mM arginine are co-utilized, the production is even increased with less CO uptake, demonstrating that arginine supplementation improves carbon efficiency to a target molecule.

Example 6

Use of Arginine Repressor as Genetic Switch to Drive Expression of Heterologous Pathways This example demonstrates that arginine can be used as genetic switch to drive expression of heterologous pathways.

All genes in identified arginine deaminase pathway of example 3 were found to be clustered together and also an arginine repressor ArgR was found. Operator sequences (DNA sequences to which the argR protein binds in order to prevent gene transcription) have been identified in a range of microorganisms including *E. coli* (Tian et al. 1992, J. Mol. Biol. 226, pp. 387-397) and the binding site is generally conserved across bacterial lineages (Makarova et al. 2001, Genome Biol. 2, pp 1-8).

The arginine repressor controls gene expression by binding to a palindromic operator sequence that is located approximately 45 bp upstream of the arginine deiminase start codon. Addition of arginine causes the repressor to unbind the operator sequence, allowing transcription of the genes downstream of the operator sequence. In a prophetic example, heterologous gene expression can be activated by addition of arginine. Heterologous gene expression will be repressed by the argR protein if the argR-binding operator sequence is added to the upstream region of heterologous genes. Subsequently, gene expression can be activated by addition of arginine.

In one example the heterologous genes may encode for a metabolic pathway that requires ATP for synthesis of the product. For example the mevalonate pathway is a heterologous pathway that converts acetyl-CoA to isopentenyl-diphosphate at a cost of 3 mol ATP per mol isopentenyl-diphosphate. Using the method described, expression of the heterologous mevalonate pathway could be activated by addition of arginine, which would also provide ATP for the mevalonate pathway through degradation of arginine via the arginine deiminase pathway.

Example 7

Optimizing Efficiency of Co-Utilization of Arginine with Gaseous Substrates CO and/or $H_2$ and/or $CO_2$ To achieve efficient co-utilization of arginine with gaseous substrates CO and/or H2 and/or CO2, it may be necessary to remove regulation. This could be either achieved by knock-out of above described arginine repressor ArgR to remove repression of the genes of the arginine deaminase pathway. Such knockouts can be achieved by someone skilled in the art using methods described before [W2012053905, WO2012115527, WO2013180584]. Removal of the arginine repressor would however, not allow to activate heterologous gene expression by addition of arginine as described above. An alternative method would be to remove above described operator binding sequences upstream of the arginine deaminase pathway operon or replace the region upstream of the arginine deaminase pathway operon including the operator sequence and promoter sequence with a constitutive or synthetic promoter. Such modifications can be achieved by someone skilled in the art using methods described before [W2012053905, WO2012115527, WO2013180584]. Suitable constitutive and synthetic promoters are for example but not limited to ferredoxin promoter Pfdx, acetate kinase promoter Ppta, or Ptet or PIPL12 that have been described before [US 20160160223; Nagaraju et al, Genome editing of *Clostridium autoethanogenum* using CRISPR/Cas9, Biotechnol Biofuels. 2016; 9: 219].

Similarly, promoter regions of genes responsible for CO and/or H2 and/or CO2 utilization such as the Wood-Ljungdahl cluster or Hyt operon (Brown et al. Comparison of single-molecule sequencing and hybrid approaches for finishing the genome of *Clostridium autoethanogenum* and analysis of CRISPR systems in industrial relevant Clostridia. Biotechnology for Biofuels 2014 7:40) can be replaced with constitutive and synthetic promoters or respective regulators knocked-out or knocked-down. Persons skilled in the art will be able to identify such regulators from transcriptomics data as described in example 10.

Example 8

Alternative Arginine Utilization Route and Production of Putrescine

This example demonstrates an alternative arginine utilization pathway that can yield putresine as by-product.

Another possible route for arginine utilization is via arginine decarboxylation instead of deamination: arginine can be decarboxylated to agmatine and CO2 by the enzyme arginine decarboxylase. Agmatine can subsequently be converted to N-carbamoyl putrescine by the enzyme agmatine deiminase, also yielding ammonium. N-carbamoyl-putrescine plus phosphate can be converted to putrescine plus carbamoyl-phosphate by putrescine carbamoyl transferase. Carbamoyl phosphate plus ADP is converted to ammonium+ ATP+CO2 by carbamate kinase via the same mechanism as in the arginine deiminase pathway. The net yield of ammonium and ATP is the same as the arginine deiminase pathway but with two different intermediates (agmatine and N-carbamoyl putrescine instead of citrulline) and a different byproduct (putrescine instead of ornithine).

Putrescince is a byproduct of greater value than either ornithine or arginine and can be used as a feedstock in the production of a variety of polymers including nylon-4,6 (Qian et al. 2009, Biotechnol. Bioeng. 104, pp. 651-662) and polyurethane (Dahiyat et al. 1993, J. Biomater. Sci. Polym. Ed., 4, pp. 529-543).

TABLE 10

| Gene names | EC number | Identifiers |
| --- | --- | --- |
| Arginine decarboxylase | EC 4.1.1.9 | AGY76455, CAETHG_2244 |
| Agmatine deiminase | EC 3.5.3.12 | AGY76293.1, CAETHG_2074 |
| Putrescine carbamoyl transferase | EC 2.3.1.6 | EKU86922, WP_003731415.1, AGY76301 |
| Carbamate kinase | EC 2.7.2.2 | AGY77835, CAETHG_3632 |

Example 9

Production of Alanine and Conversion to 3-HP or Acrylic Acid Via Heterologous Pathways This example demonstrates conversion of alanine to 3-hydroxypropionate or acrylic acid.

Production of alanine from arginine by *C. autoethanogenum* has been demonstrated in example 1. Alanine may be further converted into high value products 3-hydroxypropionate (3-HP) or acrylic acid.

Conversion of alanine to acrylate has been shown in *Clostridium propionicum* (Dalal R K, Akedo M, Cooney C L, Sinskey A J (1980) A microbial route for acrylic acid production. Biosources Dig 2:89-97). Conversion can either proceed via malonyl-semialdehyde and 3-HP, or via alanyl-CoA. Both 3-HP and alanyl-CoA can be converted to acrylyl-CoA and further to acrylate. Isolated genes/enzymes of *C. propionicum* may be introduced and heterologously expressed by someone skilled in the art using methods described before to produce 3-hydroxypropionate or acylate [W2012053905, WO2012115527, WO2013180584].

Example 10

Transcriptome Analysis

Transcriptome analysis of biological duplicate *C. autoethanogenum* bioreactor cultures growing heterotrophically on 4AA medium see table 2 for details) was conducted using RNA-sequencing. During the balanced growth phase and uptake of all 4AAs, approximately 35 mL of 0.3 gDCW/L culture was collected, pelleted (5000×g for 3 min at 4° C.) and resuspended in 5 mL of RNAlater (Qiagen). The sample was stored at 4° C. overnight, centrifuged (4000×g for 10 min at 4° C.) and the pellet stored at −80° C. until further processing. Frozen pellets were thawed, total RNA extracted, and mRNA libraries prepared as described in Marcellin et al., 2013. Sequencing was performed using an Illumina Hiseq-2000 sequencer.

Gene expression patterns on 4AA medium were compared against RNA-seq data of the same *C. autoethanogenum* strain (DSM 10061) grown heterotrophically on standard PETC-MES (including YE) and published previously (Marcellin et al., 2016). Sequencing reads of both heterotrophic conditions were trimmed to avoid reading errors and then aligned/realigned to the genome using TopHat2 (Kim et al., 2013) with two mismatches allowed per read alignment. Transcript abundances were estimated using the FPKM function from Cufflinks using upper quartile normalisation. CuffDiff was used to estimate differentially expressed transcripts, and Cuffnorm was used for data normalisation. A q-value lower than 0.05 (using false discovery rate; Benjamini and Hochberg, 1995) was used to determine significant gene expression changes.

Transcriptome analysis using RNA-sequencing (RNA-seq) was performed to further get confirmatory evidence for ADI pathway involvement at gene expression level. For this, biological duplicate *C. autoethanogenum* bioreactor cultures growing heterotrophically on 4AA medium were sampled during the balanced growth phase. This RNA-seq dataset was compared to the previously published dataset (Marcellin et al., 2016) of the same *C. autoethanogenum* strain (DSM 10061) grown heterotrophically (fructose) on the standard YE-containing PETC-MES medium.

Transcriptome analysis proved the role of the ADI pathway as all ADI pathway genes were more than 500-fold up-regulated (q-values of <0.001) when cells were grown on PETC-MES supplemented with 4AA compared to YE.). In addition, more than 380-fold up-regulation (q-values of <0.001) of putative arginine-ornithine antiporter genes (CAETHG_3023 and 3024) was observed. From the four genes associated with citrulline degradation into carbamoyl-phosphate and ornithine in *C. autoethanogenum* our data indicate that ornithine carbamoyltransferase (CAETHG 3022) is the flux-catalysing protein (645-fold up-regulation; q<0.001) during ARG catabolism in *C. autoethanogenum* as its isoenzymes were either down-regulated (CAETHG_0449 and 0591) or showed no change (CAETHG_2082) between the conditions compared. Similarly, from the five genes associated with carbamoyl-phosphate degradation into CO2, the carbamate kinase of CAETHG_3025 seems to be the flux-catalysing protein (623-fold up-regulation; q<0.001) as its FPKM value is 1000-fold higher than the FPKM values for its isoenzymes.

Example 11

Optimizing Efficiency of Arginine Incorporation into the Central Metabolism

Transcriptomics analysis identified genes that in the native metabolism determine the flux of arginine utilization and incorporation into the central metabolism as ornithine carbamoyltransferase (CAETHG_3022) and carbamate kinase (CAETHG_3025). To improve efficiency, these genes can be overexpressed using strong or inducible promoters, for example but not limited to ferredoxin promoter Pfdx, acetate kinase promoter Ppta, or Ptet or PIPL12 that have been described before [US 20160160223; Nagaraju et al, Genome editing of *Clostridium autoethanogenum* using CRISPR/Cas9, Biotechnol Biofuels. 2016; 9: 219].

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for improving efficiency of arginine co-utilization with one or more gaseous substrates selected from the group consisting of CO, $H_2$ and $CO_2$, the method comprising culturing a genetically engineered C1-fixing bacterium comprising one or more genetic modifications selected from the group consisting of:
   i) a disruptive mutation in an arginine transporter;
   ii) overexpression of one or more endogenous enzymes selected from the group consisting of arginine deiminase (EC 3.5.3.6), ornithine carbomyltransferase (putrescine carbomyltransferase) (EC 2.1.3.3), carbamate kinase (EC 2.7.2.2), ornithine racemase (EC 5.1.1.12), ornithine aminomutase (EC 5.4.3.5), and 2,4-diaminopentanoate dehydrogenase (EC 1.4.1.12);
   iii) expression of one or more mutated endogenous enzymes selected from the group consisting of arginine deiminase (EC 3.5.3.6), ornithine carbomyltransferase (putrescine carbomyltransferase) (EC 2.1.3.3), carbamate kinase (EC 2.7.2.2), ornithine racemase (EC 5.1.1.12), ornithine aminomutase (EC 5.4.3.5), and 2,4-diaminopentanoate dehydrogenase (EC 1.4.1.12); and
   iv) expression of one or more exogenous enzymes selected from the group consisting of arginine deiminase (EC 3.5.3.6), ornithine carbomyltransferase (putrescine carbomyltransferase) (EC 2.1.3.3), carbamate kinase (EC 2.7.2.2), ornithine racemase (EC 5.1.1.12), ornithine aminomutase (EC 5.4.3.5), and 2,4-diaminopentanoate dehydrogenase (EC 1.4.1.12) wherein arginine is a sole nitrogen source.

2. The method of claim 1, further comprising one or more genetic modifications selected from the group consisting of (i) disruptive mutation of regulatory elements and (ii) replacement of operator binding sites or native promoters with constitutive or synthetic promoters.

3. The method of claim 2, wherein the disruptive mutation is a knock-out of arginine repressor argR.

4. The method of claim 2, wherein the replacement is a replacement of an arginine deaminase pathway operon promoter with a constitutive or synthetic promoter.

5. The method of claim 1, wherein arginine is provided to the culture in excess of a cellular requirement of the culture.

6. The method of claim 1, wherein the C1-fixing microorganism is a *Clostridium* bacterium.

* * * * *